(12) United States Patent
Hennings et al.

(10) Patent No.: US 7,524,316 B2
(45) Date of Patent: Apr. 28, 2009

(54) ENDOVENOUS CLOSURE OF VARICOSE VEINS WITH MID INFRARED LASER

(75) Inventors: David R. Hennings, Roseville, CA (US); Mitchel P. Goldman, La Jolla, CA (US); Robert A. Weiss, Hunt Valley, MD (US); Eric B. Taylor, Roseville, CA (US); Don Johnson, Roseville, CA (US); Ignacio Cespedes, Folsom, CA (US)

(73) Assignee: CoolTouch, Inc., Roseville, CA (US)

( * ) Notice: Subject to any disclaimer, the term of this patent is extended or adjusted under 35 U.S.C. 154(b) by 530 days.

(21) Appl. No.: 10/982,504

(22) Filed: Nov. 4, 2004

(65) Prior Publication Data

US 2005/0131400 A1    Jun. 16, 2005

Related U.S. Application Data

(63) Continuation-in-part of application No. PCT/US03/35178, filed on Oct. 30, 2003.

(60) Provisional application No. 60/422,566, filed on Oct. 31, 2002.

(51) Int. Cl.
*A61B 18/18* (2006.01)

(52) U.S. Cl. .................. 606/7; 606/3; 606/15; 607/88; 607/89; 128/898

(58) Field of Classification Search .................. 606/3, 606/7, 15; 607/88, 89; 128/898
See application file for complete search history.

(56) References Cited

U.S. PATENT DOCUMENTS 4,693,556 A    9/1987  McCaughan, Jr.
4,819,630 A    4/1989  DeHart
4,854,320 A *  8/1989  Dew et al. ...................... 606/3

(Continued)

FOREIGN PATENT DOCUMENTS

WO    WO 92/17243    10/1992

(Continued)

OTHER PUBLICATIONS

Goldman et al., Endovenous 1064-nm and 1320-nm ND:YAG Laser Treatment of the Porcine Greater Saphenous Vein, Cosmetic Dermatology, vol. 16, No. 2, Feb. 2003, pp. 25-28.

*Primary Examiner*—Ahmed M Farah
(74) *Attorney, Agent, or Firm*—Orrick, Herrington & Sutcliffe LLP

(57) ABSTRACT

This invention is an improved method and device for treating varicose veins 200 or the greater saphenous vein 202. The method comprises the use of infrared laser radiation in the region of 1.2 to 2.2 um in a manner from inside the vessel 200 or 202 such that the endothelial cells of the vessel wall 704 are damaged and collagen fibers in the vessel wall 704 are heated to the point where they permanently contract, the vessel 200 or 202 is occluded and ultimately resorbed. The device includes a laser 102 delivered via a fiber optic catheter 300 that may have frosted or diffusing fiber tips 308, or that may be provided with a protective spacer. A motorized pull back device 104 may be used, and a thermal sensor 600 may be used to help control the power required to maintain the proper treatment temperature.

10 Claims, 19 Drawing Sheets

U.S. PATENT DOCUMENTS

| | | | |
|---|---|---|---|
| 5,022,399 A | 6/1991 | Biegeleisen | |
| 5,104,392 A * | 4/1992 | Kittrell et al. | 606/15 |
| 5,107,513 A * | 4/1992 | Sagie et al. | 372/35 |
| 5,207,672 A | 5/1993 | Roth et al. | |
| 5,445,608 A * | 8/1995 | Chen et al. | 604/20 |
| 6,096,029 A * | 8/2000 | O'Donnell, Jr. | 606/9 |
| 6,258,084 B1 | 7/2001 | Goldman et al. | |
| 6,398,777 B1 * | 6/2002 | Navarro et al. | 606/7 |
| 6,752,803 B2 * | 6/2004 | Goldman et al. | 606/32 |
| 6,840,909 B2 * | 1/2005 | Gatto | 600/562 |
| 6,962,584 B1 * | 11/2005 | Stone et al. | 606/7 |
| 6,984,229 B2 * | 1/2006 | Neuberger | 606/15 |
| 6,986,766 B2 | 1/2006 | Caldera et al. | |
| 7,273,478 B2 * | 9/2007 | Appling et al. | 606/15 |
| 2004/0010248 A1 * | 1/2004 | Appling et al. | 606/15 |
| 2004/0092913 A1 * | 5/2004 | Hennings et al. | 606/3 |
| 2005/0015123 A1 | 1/2005 | Paithankar | |
| 2005/0288655 A1 | 12/2005 | Root et al. | |
| 2007/0179486 A1 | 8/2007 | Welch et al. | |

FOREIGN PATENT DOCUMENTS

WO     WO 93/15664     8/1993

\* cited by examiner

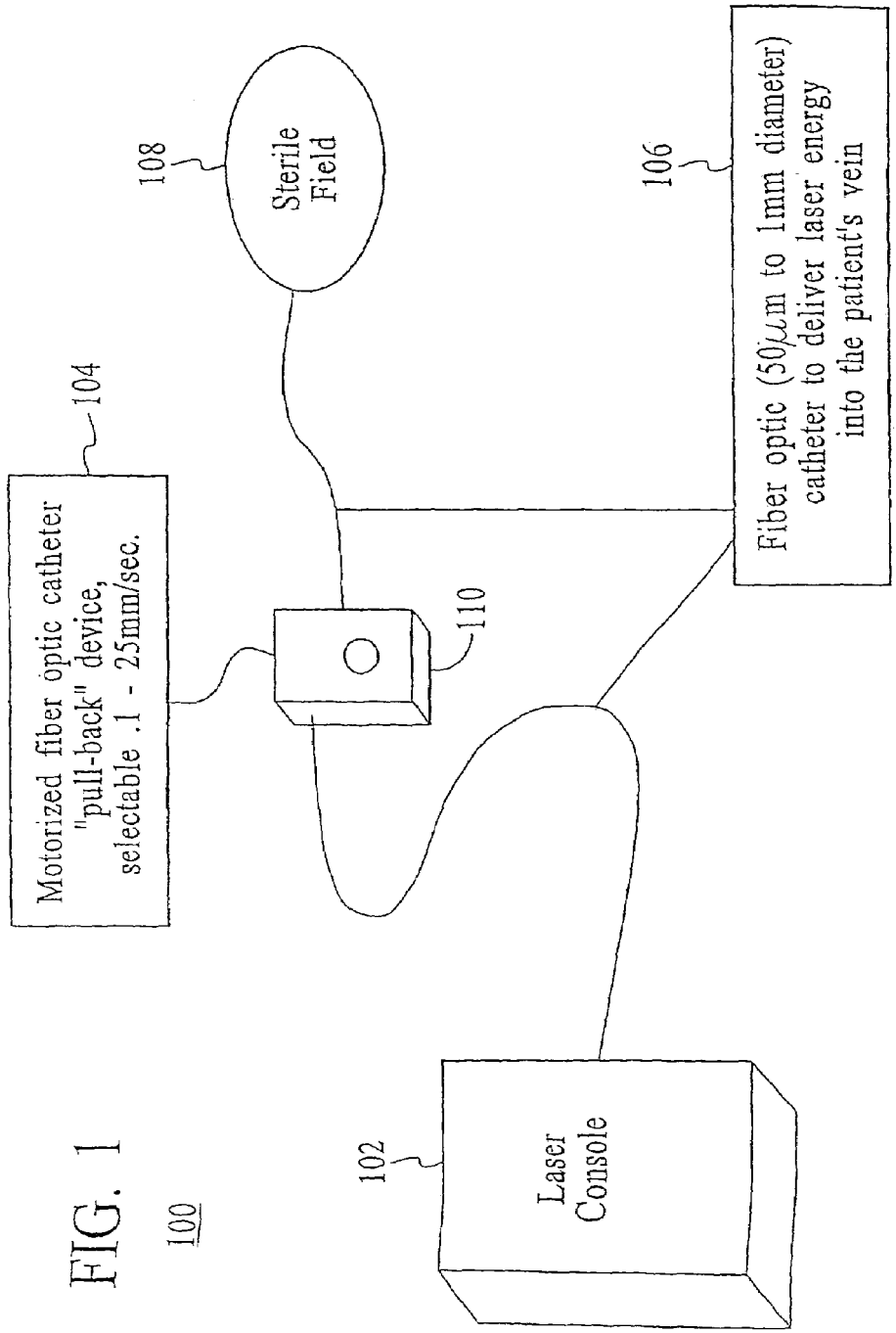

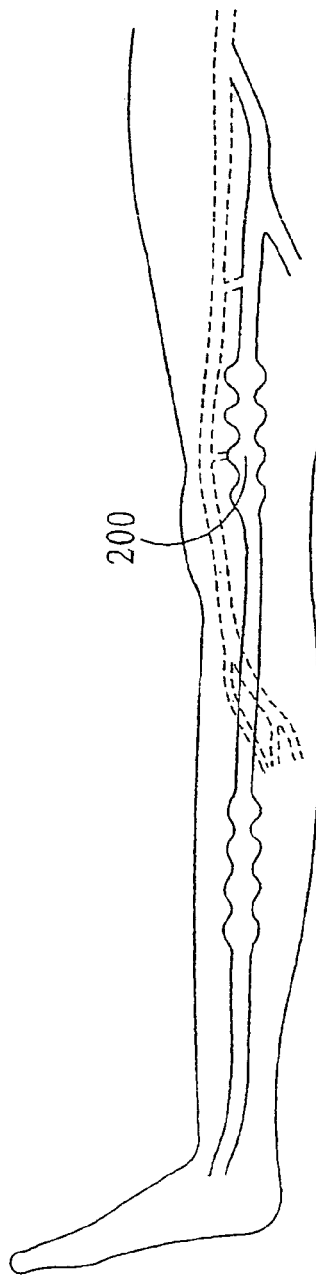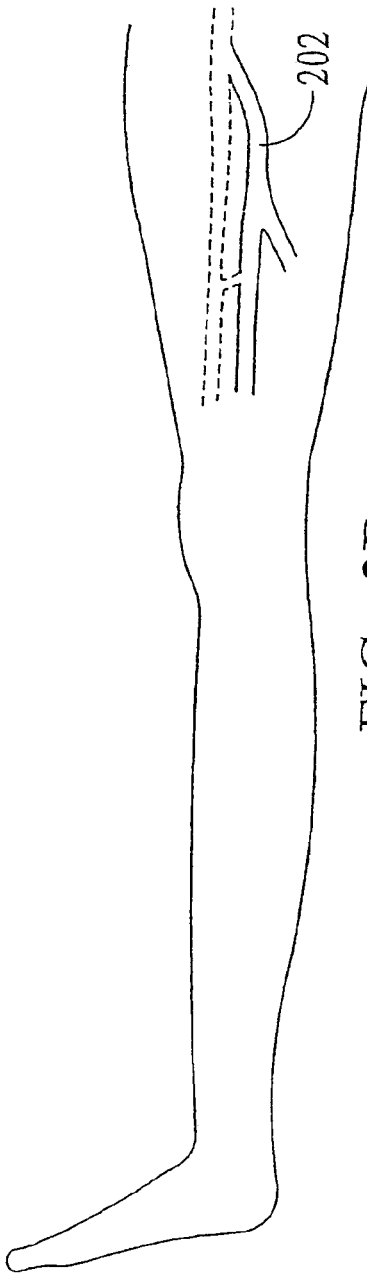
FIG. 2A
FIG. 2B

ENDOVENOUS CLOSURE OF VARICOSE VEINS WITH MID INFRARED LASER

RELATED APPLICATIONS

This Application is a continuation-in-part of and claims the benefit of International Application Number PCT/US2003/035178, filed under the Patent Cooperation Treaty on Oct. 30, 2003, designating the United States of America, and titled "ENDOVENOUS CLOSURE OF VARICOSE VEINS WITH MID INFRARED LASER," which application claims the benefit of U.S. Provisional Patent Application Ser. No. 60/422,566 filed Oct. 31, 2002, entitled ENDOVENOUS CLOSURE OF VARICOSE VEINS WITH MID INFRARED LASER, each of which is incorporated herein by reference in its entirety.

FIELD OF THE INVENTION

The present invention relates generally laser assisted method and apparatus for treatment of varicose veins, and more particularly, to an improved catheter method and apparatus to target blood vessel walls directly and with a controlled amount of the appropriate type of energy using a motorized pull-back device, and to improved methods and apparatus for substantially preventing direct physical contact between the vessel walls and the source of laser energy.

BACKGROUND OF THE INVENTION

Most prior techniques to treat varicose veins have attempted to heat the vessel by targeting the hemoglobin in the blood and then having the heat transfer to the vessel wall. Lasers emitting wavelengths of 500 to 1100 nm have been used for this purpose from both inside the vessel and through the skin. Attempts have been made to optimize the laser energy absorption by utilizing local absorption peaks of hemoglobin at 810, 940, 980 and 1064 nm. RF technology has been used to try to heat the vessel wall directly but this technique requires expensive and complicated catheters to deliver electrical energy in direct contact with the vessel wall. Other lasers at 810 nm and 1.06 um have been used in attempts to penetrate the skin and heat the vessel but they also have the disadvantage of substantial hemoglobin absorption which limits the efficiency of heat transfer to the vessel wall, or in the cases where the vessel is drained of blood prior to treatment of excessive transmission through the wall and damage to surrounding tissue. All of these prior techniques result in poor efficiency in heating the collagen in the wall and destroying the endothelial cells.

Baumgardner and Anderson teach the advantages of using the mid IR region of optical spectrum 1.2 to 1.8 um, to heat and shrink collagen in the dermis.

The prior art teaches manual retraction of the catheter. This is a major cause of overheating and perforation of the vessel wall as even the best surgeon may have difficulty retracting the fiber at exactly the correct speed to maintain a vessel wall heating temperature of 85 deg C. Other prior art using thermocouples at the tip of the catheter depend on electrical contact between electrodes inside the vessel and are expensive and require very slow catheter-withdrawal (2 cm/min.) and are difficult to use.

The relevant references in the prior art teach use of much higher power levels, such as between about 10 to about 20 watts. This is because the prior art laser wavelengths are not as efficiently coupled to the vessel wall and are instead absorbed in the blood or transmitted through the wall into surrounding tissue. It will be understood that methods taught in the prior art can be inefficient to such a degree that external cooling is mandatory on the skin surface to prevent burns.

Finally, the methods and apparatus taught in the prior art does not mention the use of diffusing catheter tips for varicose vein treatment. Use of common, standard, non-diffusing tip fiber optic and other laser delivery devices increases the risk for perforation of the cannulated vessel.

Navarro et al., U.S. Pat. No. 6,398,777 issued Jun. 4, 2002, teaches a device and method of treating varicose veins that involves using laser energy whose wavelength is 500 to 1100 nm and is poorly absorbed by the vessel wall. Laser energy of wavelengths from 500 to 1100 nm will penetrate 10 to 100 mm in tissue unless stopped by an absorbing chromophore. See FIG. X. Most of the energy used by this method passes through the vessel wall and causes damage to surrounding tissue. Procedures using these wavelengths can require cooling of the surface of the leg to prevent burning caused by transmitted energy. Operative complications of this technique include bruising and extensive pain caused by transmitted energy and damage to surrounding tissue.

However, this technique does appear to be clinically effective (but misleadingly so) because the blood that remains in the vein after compression absorbs the 500 to 1100 nm energy. 500 to 1100 nm light is absorbed in less than 1 mm in the presence of hemoglobin. See FIG. 10. This blood heats up and damages the vein wall by conduction, not by direct wall absorption as claimed by Navarro.

This prior art technique is poorly controlled because the amount of residual blood in the vein can vary dramatically. During an actual procedure using 500 to 1100 nm lasers it is possible to see the effects of blood absorption of the energy. At uncontrolled intervals white flashes will be seen indicating places of higher blood concentration. The blood can boil and explode in the vessel causing occasional perforation of the vein wall and unnecessary damage to healthy tissue.

In places without residual blood the laser energy has no absorbing chromophore and will be transmitted through the wall without causing the necessary damage and shrinkage claimed by the inventors.

Navaro states that the treatment device described must be in direct "intraluminal contact with a wall of said blood vessel". This is necessary because the 500 to 1100 nm laser cannot penetrate any significant amount of blood, even though it requires a thin layer of blood to absorb and conduct heat to the vessel wall. This is very difficult to achieve and control.

Navarro also describes the delivery of energy in bursts. This is required using their technique because they have no means to uniformly control the rate of energy delivered. Navarro teaches a method of incrementally withdrawing the laser delivery fiber optic line while a laser burst is delivered. In clinical practice this is very difficult to do and results in excessive perforations and complications.

Closure of the greater saphenous vein (GSV) through an endolumenal approach with radiofrequency (RF) or lasers has been proven to be safe and effective in multiple studies. These endovenous occlusion techniques are less invasive alternatives to saphenofemoral ligation and/or stripping. They are typically performed under local anesthesia with patients returning to normal activities within 1-2 days.

RF energy can be delivered through a specially designed endovenous electrode with microprocessor control to accomplish controlled heating of the vessel wall, causing vein shrinkage or occlusion by contraction of venous wall collagen. Heating is limited to 85 degrees Celsius avoiding boiling, vaporization and carbonization of tissues. In addition, heating the endothelial wall to 85 degrees Celsius results in heating the vein media to approximately 65 degrees Celsius which has been demonstrated to contract collagen. Electrode mediated RF vessel wall ablation is a self-limiting process. As coagulation of tissue occurs, there is a marked decrease in impedance that limits heat generation.

Presently available lasers to treat varicose veins endoluminally heat the vessel by targeting the hemoglobin in the blood with heat transfer to the vessel wall. Lasers emitting wavelengths of 500 to 1064 nm have been used for this purpose from both inside the vessel and through the skin. Attempts have been made to optimize the laser energy absorption by utilizing local absorption peaks of hemoglobin at 810, 940, 980 and 1064 nm. The endovenous laser treatment (EVLT™) of the present invention allows delivery of laser energy directly into the blood vessel lumen in order to produce endothelial and vein wall damage with subsequent fibrosis. It is presumed that destruction of the GSV with laser energy is caused by thermal denaturization. The presumed target is intravascular red blood cell absorption of laser energy. However, thermal damage with resorption of the GSV has also been seen in veins emptied of blood. Therefore, direct thermal effects on the vein wall probably also occur. The extent of thermal injury to tissue is strongly dependent on the amount and duration of heat the tissue is exposed to. When veins are, devoid of blood, vessel wall rupture occurs.

One in vitro study model has predicted that thermal gas production by laser heating of blood in a 6 mm tube results in 6 mm of thermal damage. This study used a 940-nm-diode laser with multiple. 1 5Jr~second pulses to treat the GSV. Histologic examination of one excised vein demonstrated thermal damage along the entire treated vein with evidence of perforations at the point of laser application described as "explosive-like" photo-disruption of the vein wall. Since a 940 nm laser beam can only penetrate 0.03 mm in blood (17), the formation of steam bubbles is the probable mechanism of action.

Initial reports have shown endovenous RF to have excellent short-term efficacy in the treatment of the incompetent GSV, with 96% or higher occlusion at 1-3 years with a less than 1% incidence of transient paresthesia or erythema (10-11) Although most patients experience some degree of post-operative ecchymosis and discomfort, no other major or minor complications have been reported.

Patients treated with EVLT have shown an increase in post-treatment purpura and tenderness. Most patients do not return to complete functional normality for 2-3 days as opposed to the 1 day "down-time" with RF Closure™ of the GSV. Since the anesthetic and access techniques for the two procedures are identical, it is believed that non-specific perivascular thermal damage is the probable cause for this increased tenderness. In addition, recent studies suggest that pulsed laser treatment with its increased risk for vein perforation may be responsible for the increase symptoms with EVLT vs. RF treatment. Slow uncontrolled pull-back of the catheter is likely one cause for overheating and perforation of the vessel wall as even the best surgeon may have difficulty retracting the fiber at exactly the correct speed to maintain a vessel wall heating temperature of 85 deg C. This technique prevents damage to surrounding tissue and perforation of the vessel.

ADVANTAGES AND SUMMARY OF THE INVENTION

In a first aspect, this invention includes a method and device to treat varicose veins by targeting the vessel wall directly with a more appropriate wavelength of laser light and controlling that energy precisely using a motorized pull back device, using diffuse fiber delivery systems and utilizing thermal feedback of the treated tissue. This technique allows less energy to be used and helps prevent damage to surrounding tissue and perforation of the vessel.

It is an object and an advantage of the present invention to provide an improved method and device that uses a laser wavelength that transmits through any residual blood in the vessels and is absorbed by the water and collagen of the vessel wall. This new technique is more predictable and controllable in the presence of residual blood and is more effective in targeting only the vessel wall.

Clinical experiments have demonstrated that perforation of the vessel wall does not occur using 1.2 to 1.8 um energy, even if the fiber remains at one location for several seconds. This is because the laser energy is uniformly and predictably absorbed without any hot spots, boiling, or explosions caused by blood pockets.

Clinical experiments have demonstrated a much lower incidence of pain and collateral bruising using 1.2 to 1.8 um laser energy because the vessel wall always stops the energy. Very little transmits outside the vessel to cause damage.

Clinical experiments have demonstrated the coagulation of side vessels concurrently with larger vessel treatment due to a wave guiding effect of the 1.2 to 1.8 um laser energy into the smaller vessels. This has not been observed using 500 to 1100 nm laser energy because residual blood will absorb and stop any energy from getting into the branch vessels.

The present improved device and method in contrast to the teachings of the prior art does not require direct intraluminal contact with the vessel wall because it is less affected by residual blood. The energy passes through the residual blood without boiling or exploding and is absorbed primarily by the vessel wall. This is a significant clinical improvement over the methods of the prior art, with much better control and predictability.

The present improved device and method may utilize a continuously running laser and energy delivery with a continuous controlled withdrawal rate using a motorized pull back device.

Clinical results have shown this device and method to be clearly superior. It is easier to do for less experienced surgeons and helps eliminate perforations, pain and bruising.

In another aspect, the present invention provides a blood vessel treatment device that includes an optic fiber adapted for insertion into and treatment of a blood vessel and a laser energy source operatively coupled to the optic fiber. The optic fiber has proximal and distal ends and has an energy emitting tip at its distal end. The optic fiber preferably has a numerical aperture value of between about 0.12 to about 0.30.

In yet another aspect, the present invention provides another blood vessel treatment device that includes an optic fiber adapted for insertion into and treatment of a blood vessel and a laser energy source operatively coupled to the optic fiber. The optic fiber has proximal and distal ends and has an energy emitting tip at its distal end. The optic fiber preferably has a spacer attached to it near its distal end, the spacer adapted to substantially prevent the tip of the optic fiber from directly contacting the blood vessel during treatment.

In yet another aspect, the present invention provides a method for treating a blood vessel using laser energy that includes the steps of inserting a laser-emitting member into a blood vessel, the laser-emitting member comprising an optic fiber having a numerical aperture value of between about 0.12 to about 0.30, then placing the laser-emitting member at a treatment site within the blood vessel, and then emitting laser energy into the blood vessel through the laser-emitting member.

In yet another aspect, the present invention provides a method for treating a blood vessel using laser energy that includes the steps of inserting a laser-emitting member into a blood vessel, the laser-emitting member comprising an optic fiber having proximal and distal ends and having an energy emitting tip at its distal end, the optic fiber further having a spacer attached to its distal end, the spacer adapted to substantially prevent the tip of the optic fiber from directly contacting the blood vessel during treatment, then placing the laser-emitting member at a treatment site within the blood vessel, and then emitting laser energy into the blood vessel through the laser-emitting member.

Numerous other advantages and features of the present invention will become readily apparent from the following detailed description of the invention and the embodiments thereof, from the claims and from the accompanying drawings.

BRIEF DESCRIPTION OF THE DRAWINGS

FIG. 1 is a representative schematic block diagram of a preferred embodiment of the apparatus 100 of the present invention for performing a preferred embodiment of the varicose vein closure procedure of the present invention.

FIG. 2A is a representative view of varicosed veins 200 to be treated according to the preferred embodiment of the method and apparatus of the present invention.

FIG. 2B is a representative-view of the GSV 202 to be treated according to the preferred embodiment of the method and apparatus of the present invention.

DETAILED DESCRIPTION OF THE PREFERRED EMBODIMENT

Figure 3A:
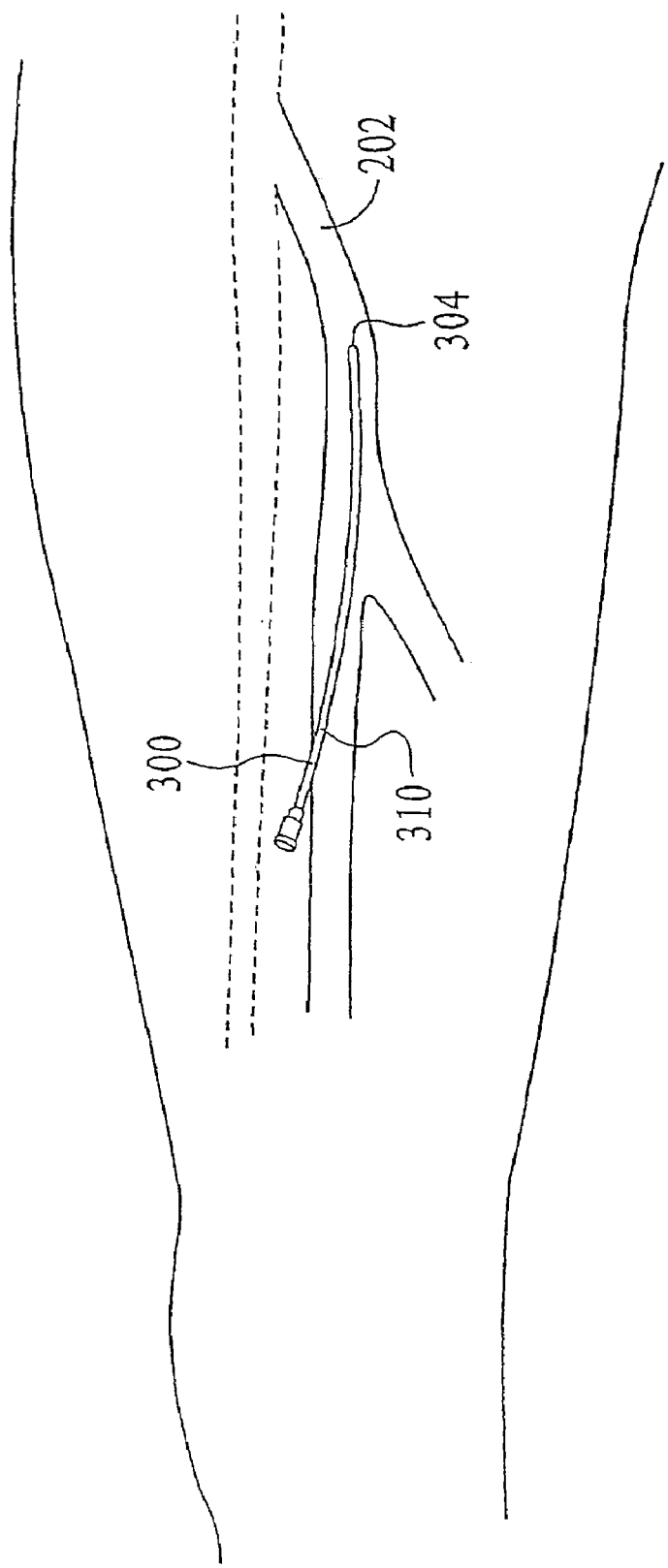
FIG. 3A is a representative view showing the beginning of the introducer or dilator 300 for percutaneous access according to the preferred embodiment of the method and apparatus of the present invention.

The description that follows is presented to enable one skilled in the art to make and use the present invention, and is provided in the context of a particular application and its requirements. Various modifications to the disclosed embodiments will be apparent to those skilled in the art, and the general principals discussed below may be applied to other embodiments and applications without departing from the scope and spirit of the invention. Therefore, the invention is not intended to be limited to the embodiments disclosed, but the invention is to be given the largest possible scope which is consistent with the principals and features described herein.

It will be understood that in the event parts of different embodiments have similar functions or uses, they may have been given similar or identical reference numerals and descriptions. It will be understood that such duplication of reference numerals is intended solely for efficiency and ease of understanding the present invention, and are not to be construed as limiting in any way, or as implying that the various embodiments themselves are identical.

FIG. 1 is a representative schematic block diagram of a preferred embodiment of the apparatus 100 of the present invention for performing a preferred embodiment of the varicose vein closure procedure of the present invention. As shown, the system 100 of the present invention includes a laser console 102, a motorized, fiber optic catheter "pull-back" machine 104, a fiber optic catheter or other laser delivery device 106 to deliver laser energy into the patient's vein, a sterile field 108 and a controller 110.

Figure 3B:
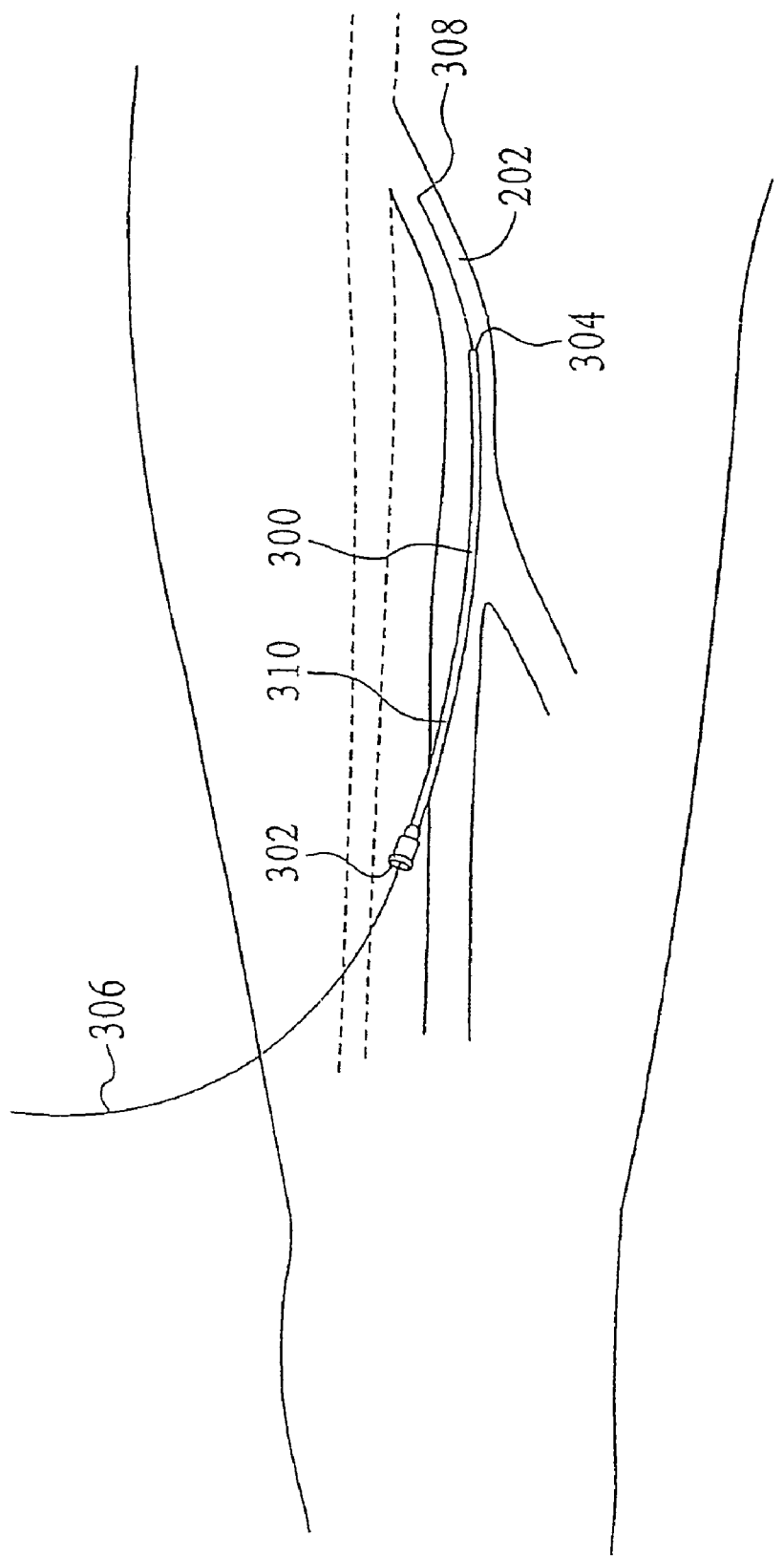
FIG. 3B is a representative view showing the use of the introducer or dilator 300 with the laser fiber 306 passing through the lumen 302 of the dilator 300 and into the GSV 202 according to the preferred embodiment of the method and apparatus of the present invention.

FIG. 2A is a representative view of varicosed veins 200 to be treated according to the preferred embodiment of the method and apparatus of the present invention. FIG. 2B is a representative view of the GSV 202 to be treated according to the preferred embodiment of the method and apparatus of the present invention. FIG. 3A is a representative view showing the beginning of the introducer or dilator 300 for percutaneous access according to the preferred embodiment of the method and apparatus of the present invention. FIG. 3B is a representative view showing the use of the introducer or dilator 300 with the laser fiber 306 passing through the lumen 302 of the dilator 300 and into the GSV 202 according to the preferred embodiment of the method and apparatus of the present invention.

Figure 4:
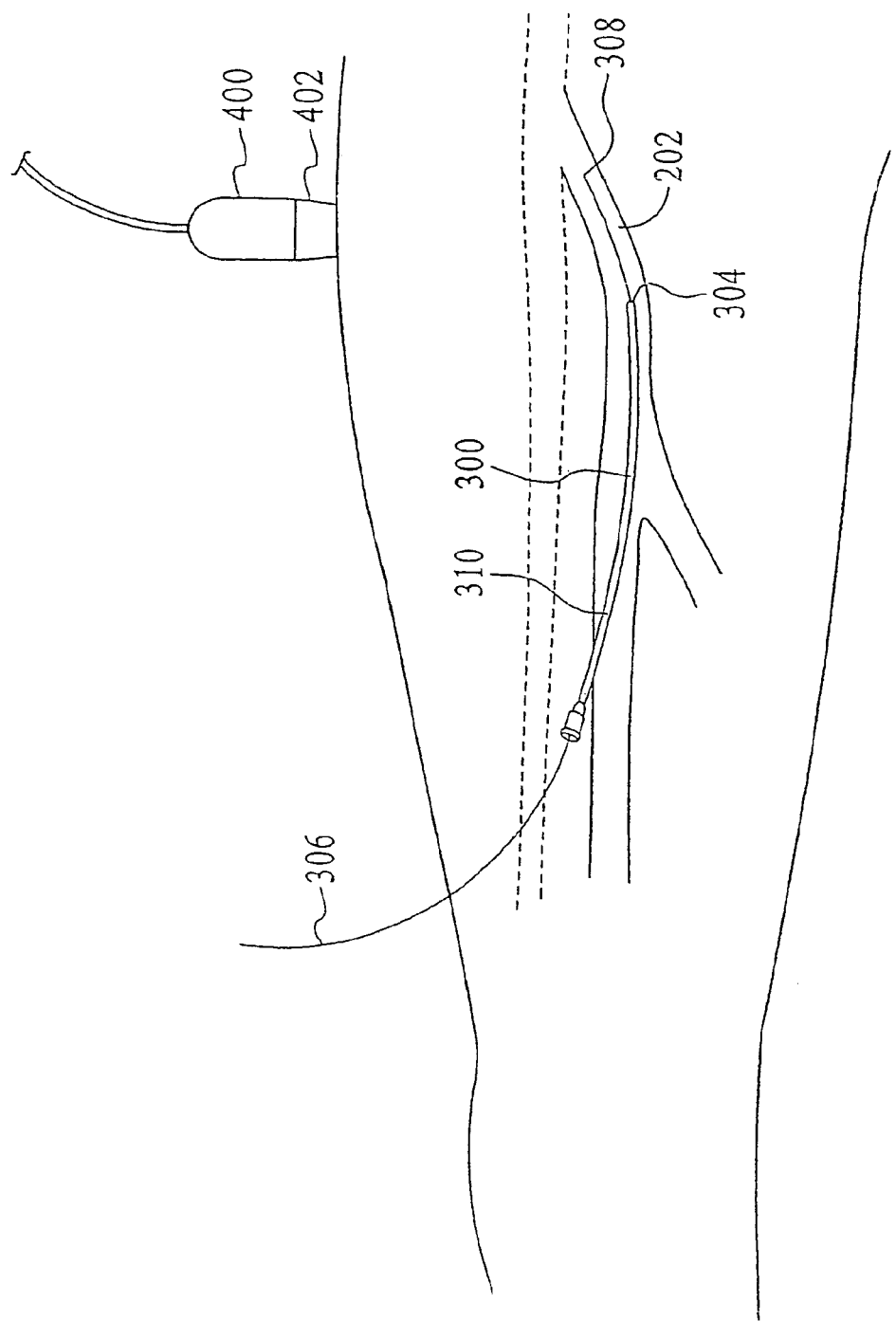
FIG. 4 is a representative view of the use of an ultrasound device 400 according to the preferred embodiment of the method and apparatus of the present invention.
Figure 5:
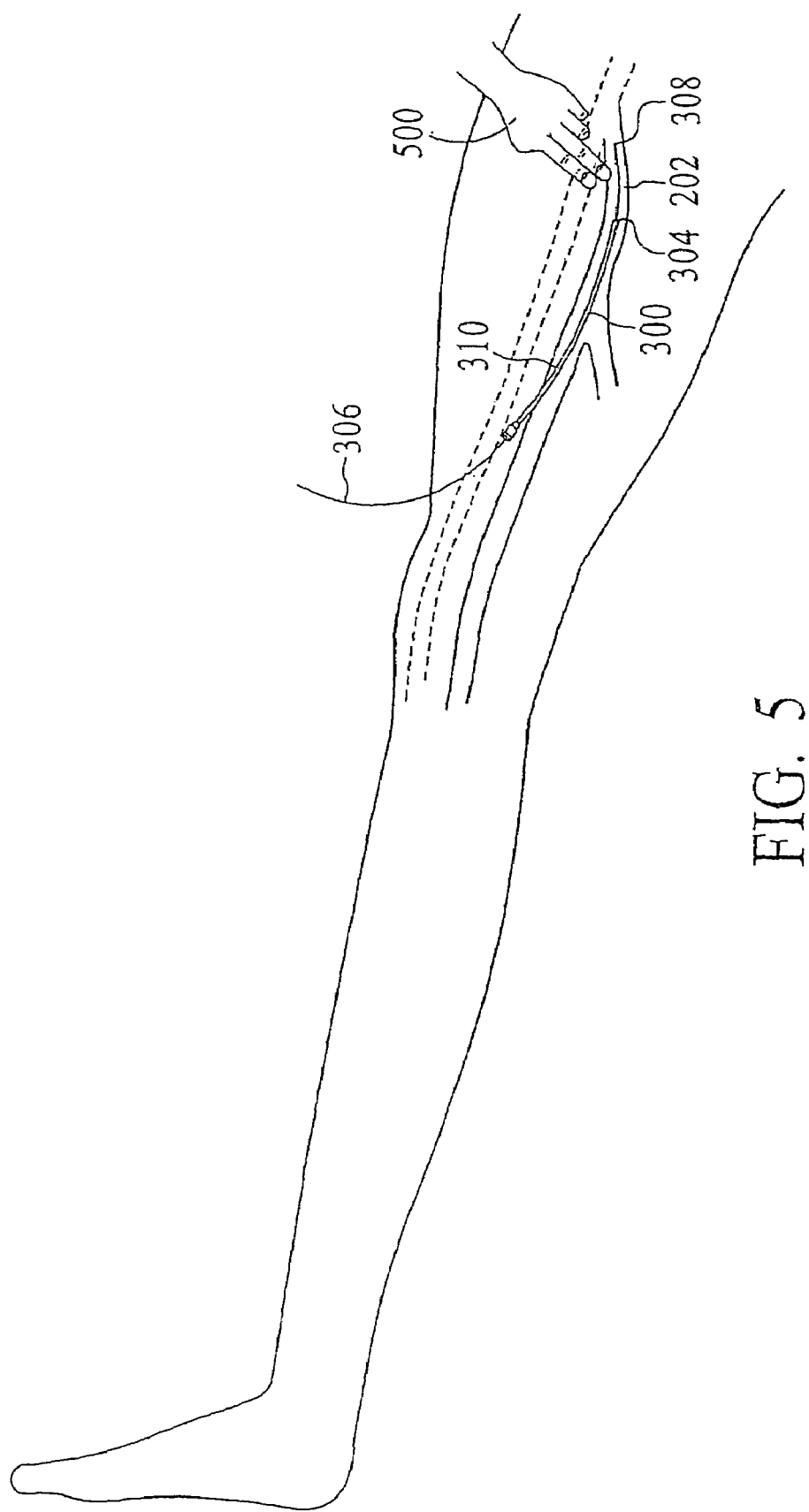
FIG. 5 is a representative view of a physician 500 performing manual compression of tissue near the tip 308 of the fiber 306 according to the preferred embodiment of the method and apparatus of the present invention.

FIG. 4 is a representative view of the use of an ultrasound device 400 according to the preferred embodiment of the method and apparatus of the present invention. FIG. 5 is a representative view of a physician 500 performing manual compression of tissue near the tip 308 of the fiber 306 according to the preferred embodiment of the method and apparatus of the present invention. As described herein, it will be understood that the means for applying mechanical compression of the tissue near the tip 308 of the fiber includes manual compression, mechanical clamps or straps, chemical or other drug-induced swelling, etc.

Figure 7:
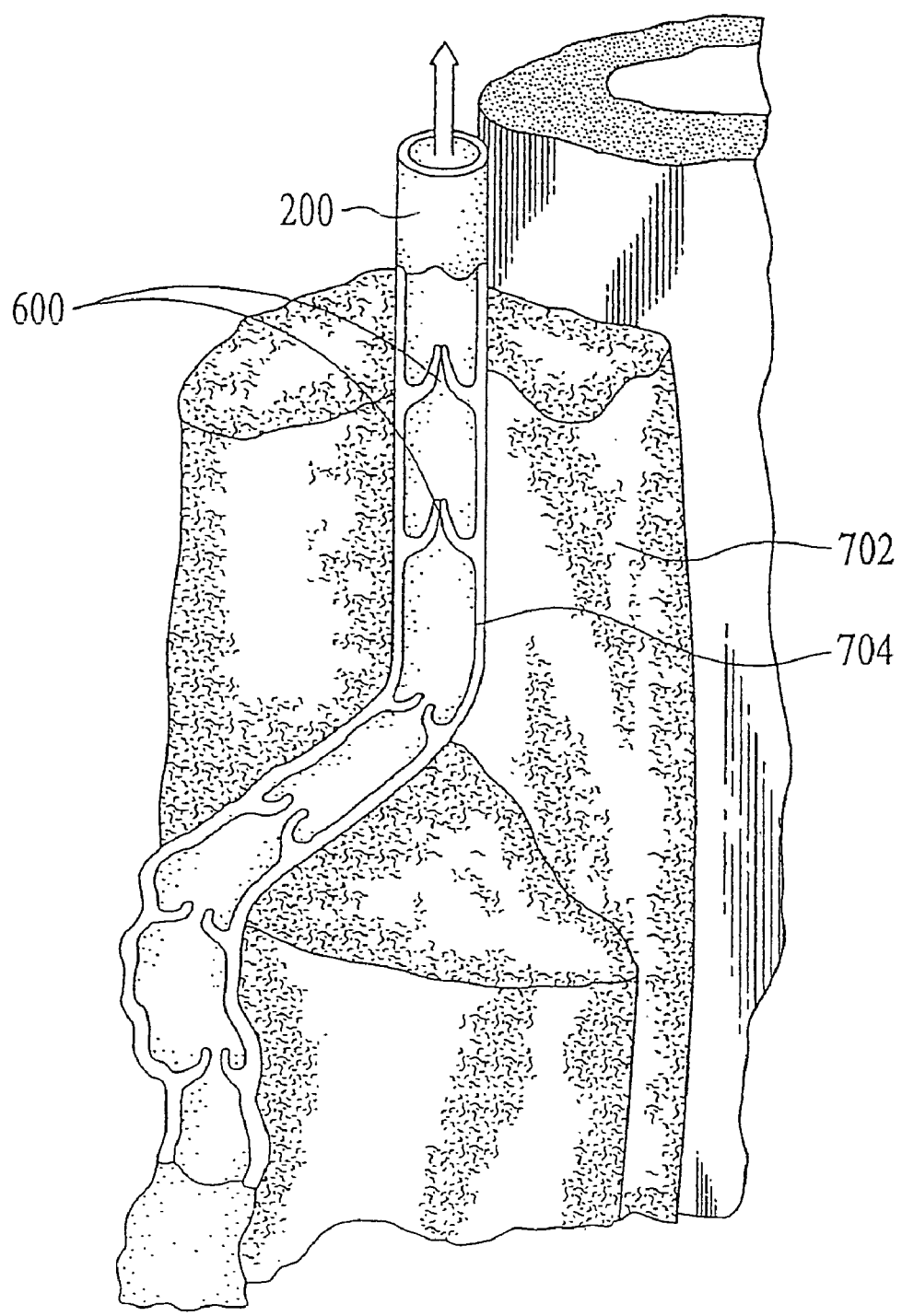
FIG. 7 is a is a representative view of a varicosed vein 200, showing prolapsed valves 690.
Figure 8:
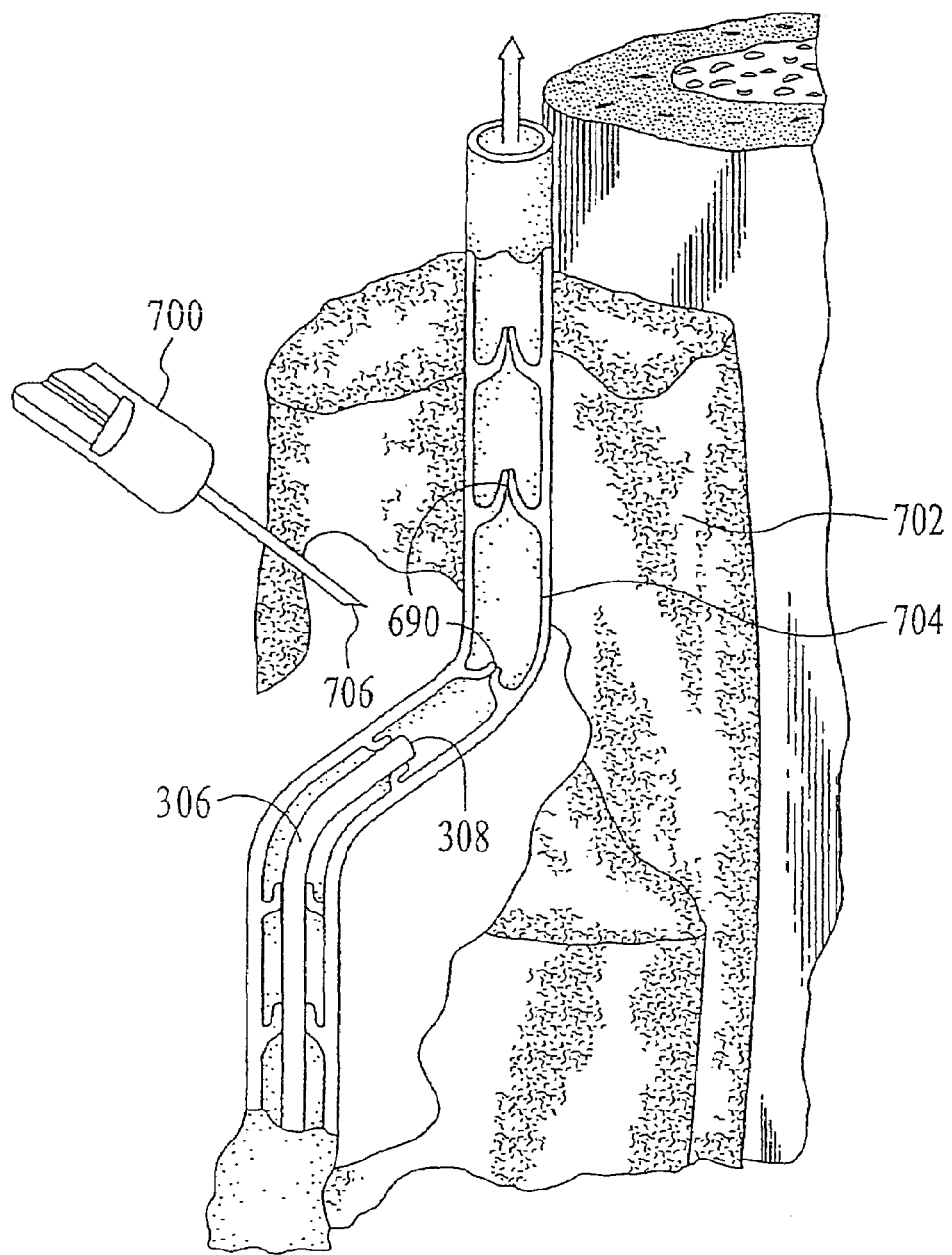
FIG. 8 is a representative view of administration of tumescent anesthesia 700 and how it compresses the vein 200 around the fiber 306 according to the preferred embodiment of the method and apparatus of the present invention.

FIG. 7 is a is a representative view of a varicosed vein 200, showing prolapsed valves 690. FIG. 8 is a representative view of administration of tumescent anesthesia 700 and how it compresses the vein 200 around the fiber 306 according to the preferred embodiment of the method and apparatus of the present invention.

Prior to treatment with the laser 102, blood is removed from the vessel 200 by using tumescent anesthesia 700, typically consisting of lidocaine 0.05 to 0.1% in normal saline. Alternate compositions for tumescent anesthesia 700 will be known to those skilled in the art. A quartz or sapphire fiber optic 306 is inserted into the vein 200 via a 16 gauge needle or similar, or through the vein 200 which has been externalized through a 2-3 mm incision with a phlebectomy hook (not shown). The fiber 306 is preferably 500 to 600 um in diameter, but fibers from 50 um to 1 mm or more or less, could be used. The fiber catheter 300 is threaded through the length of the vein 200. The position of the fiber 306 within the vein 200 is noted by observing the red aiming beam of the laser 102 as it is emitted from the tip 304 of the catheter 300 and is visible through the skin. In addition, a duplex ultrasound device 400 or similar may be used to visualize the fiber tip 308 as well as the cannulated blood vessel 200 to determine vein wall contraction and closure. In a preferred embodiment of the method of the present invention, the catheter 300 must either be removed prior to pull-back, or be secured to the fiber 306 so that both the fiber 306 and the cannula or catheter 300 are retracted simultaneously.

The catheter 300 is connected to a motorized pullback device 104 either inside or outside of the sterile field 108 of the patient. The procedure begins by starting the pull back for about 2 or 3 mm and then turning the laser 102 on at about 5 watts of power. The procedure could also be done at 1 to 20 watts of power by varying the speed of the pullback device 104.

Optical absorption curves presented by Baumgardner, Anderson, and Grove show that the primary absorbing chromophore in a vein for the 810, 940 and 1.06 um laser wavelengths is hemoglobin. When a vein is drained of blood and these lasers 102 are used, a great majority of the laser energy is transmitted through the vessel wall and heats surrounding tissue 702. The 1.2 to 1.8 um laser wavelengths are ideally suited to penetrate the small amount of remaining blood in the vessel 200 but also is much more strongly absorbed in the vessel wall 704 by collagen. Most of the energy is concentrated in the wall 704 for heating and shrinkage and is not transmitted through to surrounding tissue 702. This dramatically increases, the safety of the procedure. In addition these laser wavelength are considered more "eye" safe than the 800 to 1.06 um lasers, decreasing the risk of eye damage to the doctor and others in the operating arena.

In particular the Nd:YAG laser 102 or any other suitable, similar laser can be used. This laser 102 can operate at a wavelength of 1.32 um and can be either pulsed or continuous wave. This procedure works best when the laser 102 is continuous or pulsed at a high repetition rate to simulate a continuous output. The repetition rate for a pulsed laser 102 should be 10 Hz to 10,000 Hz.

Other lasers 102 such as Nd:YAP, ER:YAP, ER:YLF and others could be used to provide laser wavelengths in the 1.2 to 1.8 um region. These lasers 102 can be powered by optically pumping the laser crystal using a xenon or krypton flashlamp or laser diodes. They may be continuously pumped or pulsed using electro optical or acousto-optical shutters-or by pulsing the, flashlamp itself. Lasers 102 in this wavelength region also include diode lasers that emit 1.2 to 1.8 um wavelengths directly, or fiber lasers that use a length of doped fiber optic as the lasing medium.

Figure 10:
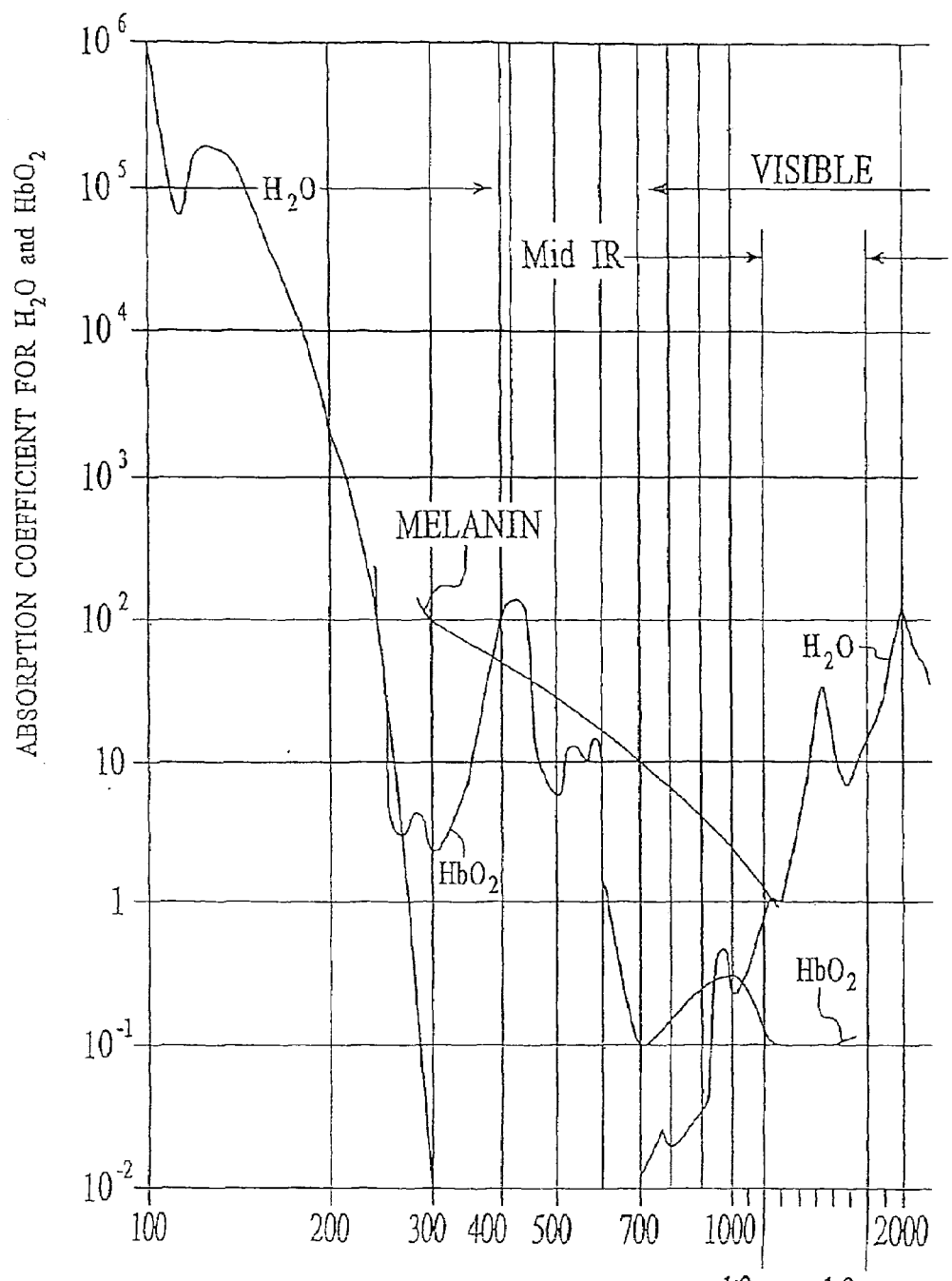
FIG. 10 shows curves for absorption coefficients of melanin, hemoglobin and water as a function of wavelength according to the preferred embodiment of the method and apparatus of the present invention.

FIG. 10 shows curves for absorption coefficients of melanin, hemoglobin and water as a function of wavelength according to the preferred embodiment of the method and apparatus of the present invention. It will be observed in FIG. 10 that the region between about 550 nm to about 1060 um shows high hemoglobin absorption and low water absorption, as is well known in the prior art technology. It will further be observed that the region between about 1200 um to about 1800 nm shows low hemoglobin and higher water absorption, which is a key to the present invention.

Figure 12:
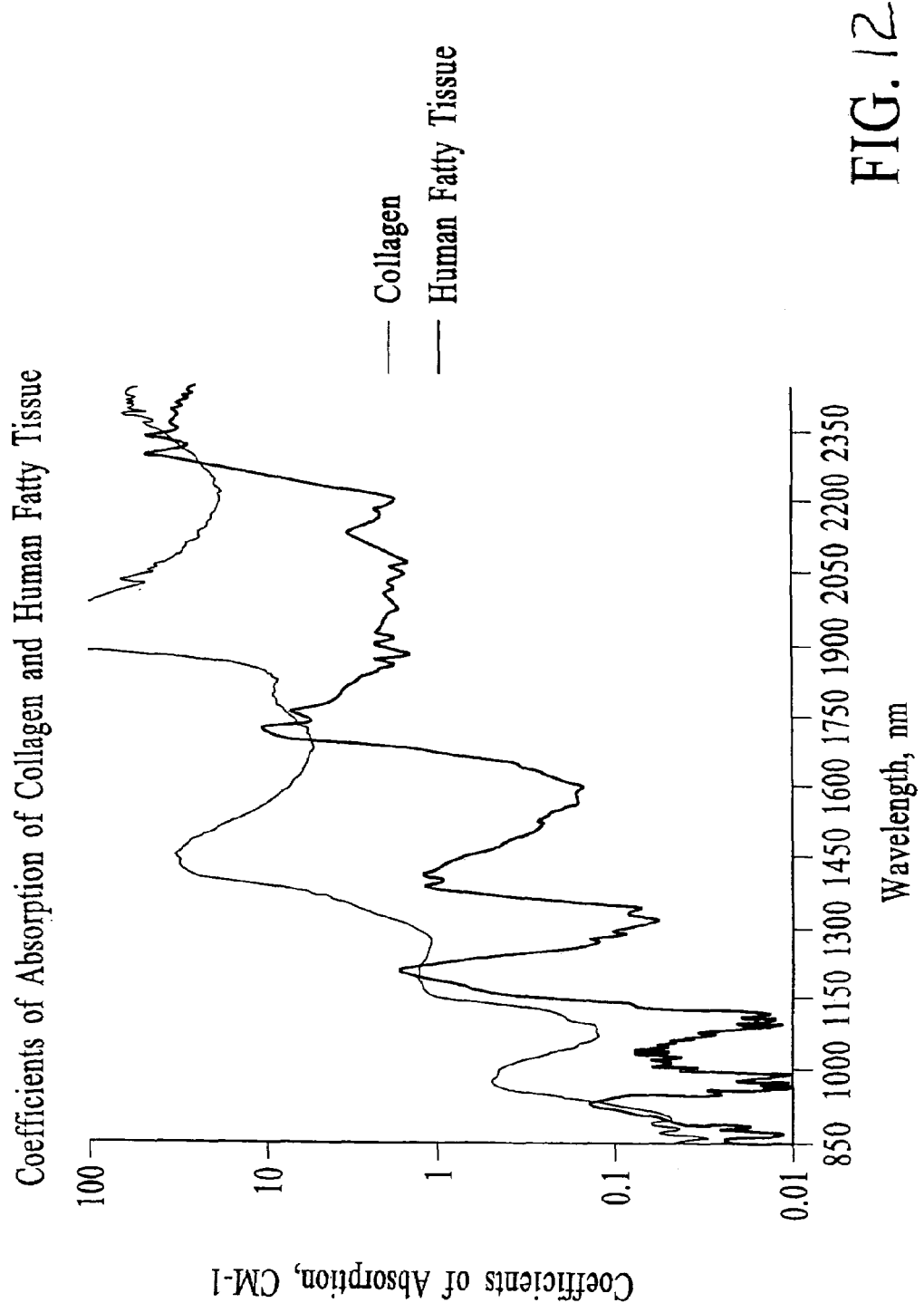
FIG. 12 is a graphical illustration showing curves for absorption coefficients of collagen and human fatty tissue as a function of energy wavelength.
Figure 13:
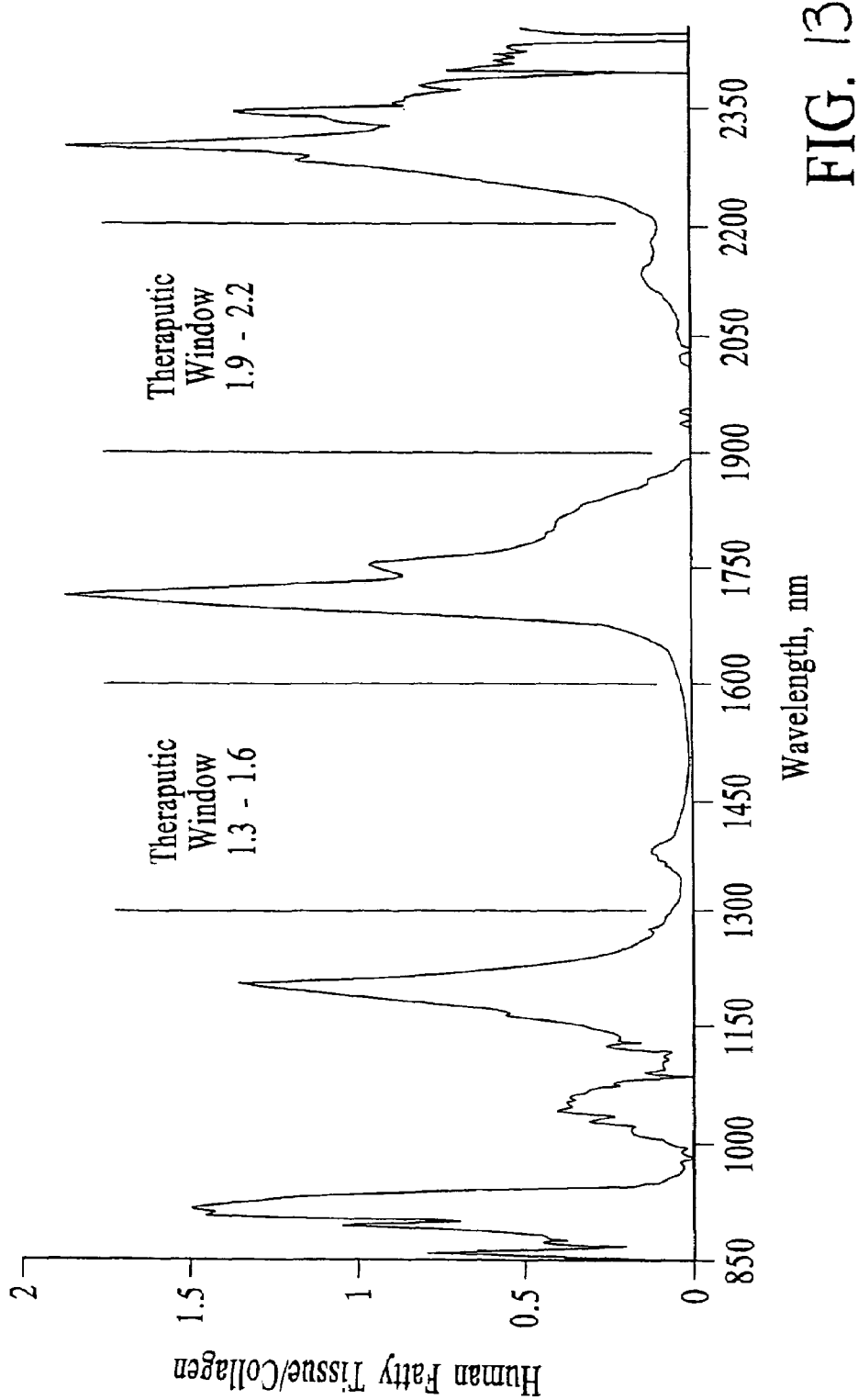
FIG. 13 is a graphical illustration showing curves for the ratio of the absorption coefficients of human fatty tissue and collagen as a function of energy wavelength.

FIG. 12 presents data comparing the coefficients of absorption of collage and of human fatty tissue as a function of radiation wavelength. It is known that human fatty tissue has a different absorption spectra than collagen, and that there are wavelength windows in that spectra where it is possible to selectively target either fat or collagen with reduced impact on the other tissue. As can be seen in the Figure, in the ranges of from about 1300 nm to about 1600 nm, and from about 1900 nm to about 2200 nm, the absorption rate of collagen is much greater than that of human fatty tissue. This characteristic is further illustrated in FIG. 13, which presents the ratio of the coefficient of absorption of human fatty tissue to that of collagen as a function of wavelength. As noted on the Figure, the ranges of 1.3-1.8 um and 1.9-2.2 um represent "therapeutic windows" in which laser energy is highly absorbed in collagen relative to human fatty tissue. The devices and methods described herein take advantage of these properties by providing laser energy having wavelengths falling within these "therapeutic window" ranges. Within these ranges, the laser energy delivered will damage the target endothelial cells within the vein wall and will do little or no damage to the tissue surrounding the vein, including very little heating of the tissue that would otherwise cause pain, swelling or purpura in the dermis.

This effect is particularly pronounced when treating small vessels because they are in such close proximity to other parts of the dermis. It has been found that laser energy with wavelengths that have absorption depths of about 0.2 to about 2 mm are best for treating small (e.g., less than 2 mm diameter) vessels. The laser wavelength range that corresponds to these absorption depths is from about 1.3 to about 1.85 um, and from about 2.1 to about 2.6 um. On the other hand, larger vessels are best treated using laser energy at wavelengths that provide absorption depths of about 1 to about 3 mm to more uniformly heat all of the endothelial tissue without the risk of hot spots and potential peroration of the vessel wall. The laser wavelengths that correspond to these longer absorption depths are from about 1.14 um to about 1.38 um. The 1.32 um Nd:YAG laser satisfies each of these ranges.

Cooling System with Thermal Feedback

The use of a thermocouple or infrared thermal detector 600 has been described for other applications, including on laser delivery fibers and for the treatment of varicose veins 202 using an radiofrequency heating device. However, by installing a thermocouple on the end of the laser delivery fiber optic device for the treatment of varicose veins, delivery of thermal energy can be more precisely controlled. In addition, in using fiber optic devices made of sapphire, a non-contact thermal sensor can be located in the laser console and measure tip temperature by measuring the black body infrared radiation profile emitted at the opposite end of the fiber reflected from the treatment site, typically via a beamsplitter in the laser console. A small-diameter sapphire fiber can be constructed that can be sterilized and re-used. Data obtained from the non-contact thermal sensor equipment 600 can also be used to either servo control delivery of the laser energy to maintain a certain temperature at the treatment site, or the control system can be used as a safety device, i.e., to terminate delivery of laser energy if a certain temperature is exceeded.

Another type of thermal feedback device 600 can be an external device that measures the heat that is transmitted out of the side of the vein 200 or 202 and heats up the surface of the skin 608 adjacent the treated vein 200 or 202. As described above, this detector can be either a contact thermocouple or a, non contact infrared detector 600. A particularly advantageous use of this type of thermal detection would be to automatically activate a cooling device 602, such as a cryogen spray, onto the skin surface 604 to keep it cool, or to send an alarm signal to the operator of the laser that too much energy is being delivered to and escaping from the treatment site. In an optional configuration, the laser operator could point an external detector at a red aiming light that is visible through the skin from the end of the treatment, fiber, similar to the use of the ultrasound device currently used, in order to control the location and duration of the delivery of the laser energy.

Figure 6:
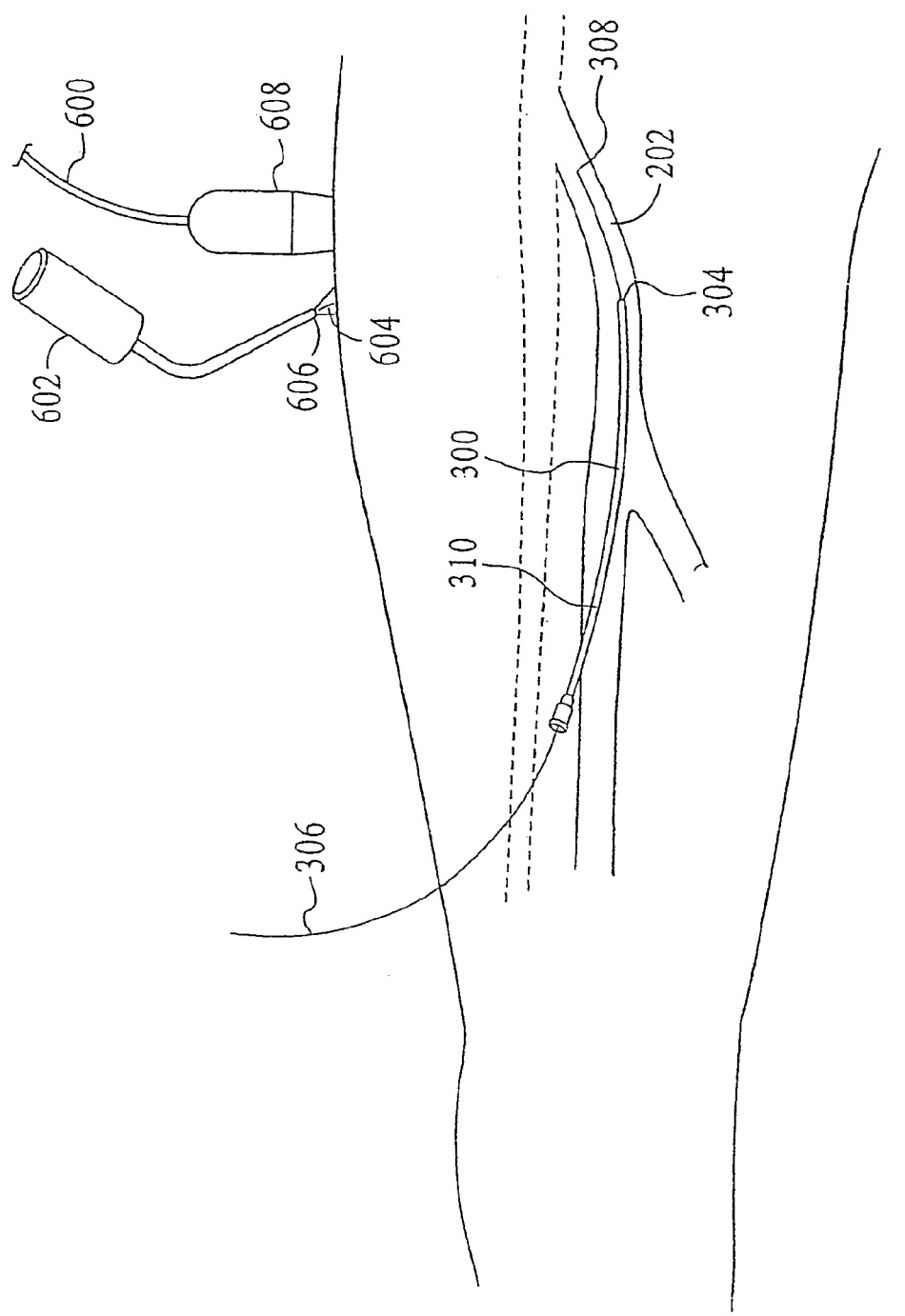
FIG. 6 is a representative view of the non-contact thermal sensor 600 and the cooling system 602 of the preferred embodiment of the method and apparatus of the present invention.

FIG. 6 is a representative view of the non-contact thermal sensor 600 and the cooling system 602 of the preferred embodimerit of the method and apparatus of the present invention. Non-contact thermal sensors 600 as well as contact devices, including RTDs, are well known in the art. It will be understood that the cooling device 602 can be any suitable, controlled device which allows a predetermined amount of cryogenic fluid to be dispensed from an on-board fluid reservoir or from an external/line source. In a preferred embodiment, the device 602 is computer controlled, to provide spurts or squirts of cryogenic fluid at a predetermined rate or for a predetermined duration. The cryogenic fluid is dispensed onto the surface of the skin 604 in an area adjacent the fluid dispensing nozzle 606, and the non-contact thermal sensor 600 determines the temperature of the skin in the same area 604 or in an area 608 distal from the area being cooled 604. The present invention, this application and any issued patent based hereon incorporates by reference the following issued patents with regards surface cooling methods and apparatus utilized in the present invention: U.S. patent application Ser. No. 08/692,929 filed Jul. 30, 1996, now U.S. Pat. No. 5,820, 626. U.S. patent application Ser. No. 938923 filed Sep. 26, 1997, now U.S. Pat. No. 5,976,123. U.S. patent application Ser. No. 10/185,490 filed Nov. 3, 1998, now U.S. Pat. No. 6,413,253. U.S. patent application Ser. No. 09/364275 filed Jul. 29, 1999, now U.S. Pat. No. 6,451,007.

Diffusing Tip Fibers

Diffusing tip fibers are well known for use with high energy lasers in other fields particularly to coagulate cancerous tumors. In addition they have been used to direct low intensity visible radiation in conjunction with photo dynamic cancer therapy. As described in the prior art, diffusing tip fibers typically require a scattering material like ceramic to be attached to the tip of a fiber in order to overcome index matching properties of the blood and liquid that the fiber is immersed into. It is frequently insufficient to abrade, roughen or shape the end of a quartz fiber by itself because the index of refraction of typical types of quartz is very close to the index of the immersing liquid, therefore any shape or structure formed in the glass or quartz portion would be ineffective in the liquid. Furthermore, in a preferred embodiment, there must be an air gap in the tip somewhere. In an alternate construction, material is selected that has bulk light scattering characteristics, like most ceramics, i.e., light is scattered as it passes through the material, as opposed to simply providing surface scattering properties. The use of diffusing tip fibers for the treatment of varicose veins is unique and has not been previously described.

Use of diffusing tip fibers for treatment of varicose veins are an improvement because the laser radiation can be directed laterally from the end of the fiber allowing more precise heating and destruction of the vein endothelial cells. Non-diffusing fiber tips direct energy along the axis of the vein and often require that the vein be compressed, in a downward position as well as around the fiber, to be most effective. The procedure described herein will work with either diffusing or non diffusing tip fibers, however, diffuse radiation will provide a more uniform and predictable shrinkage of the vein.

Adding a ceramic or quartz cap to the end of a small fiber will also aid in inserting the fiber in the vein. The cap can be made smooth and rounded so that the fiber tip does not catch on the vein or on valves within the vein as it is being inserted. A cap or smooth tip also reduces the chance of perforating the vein with a sharp fiber tip.

Figure 9A:
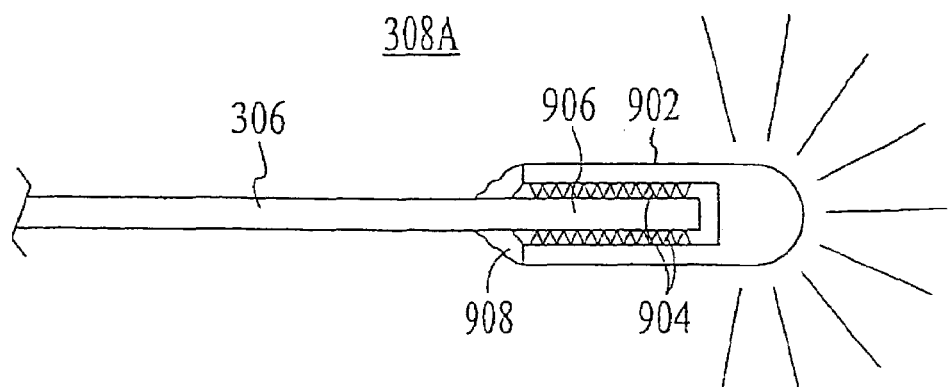
FIG. 9A is a representative view of a diffusing fiber tip according to the preferred embodiment of the method and apparatus of the present invention.

FIG. 9A is a representative view of a diffusing fiber tip 308A according to the preferred embodiment of the method and apparatus of the present invention. A ceramic or other suitable material diffusing tip 902 has an internal screw thread 904 which screws onto a buffer portion 906 of the fiber optic laser delivery device 306. The threaded portion 904 can be replaced with a clip portion or any, other suitable mechanical connection. Optionally, a non-toxic, heat-resistant- or other suitable epoxy 908 is used to permanently or removably mount the diffusing tip 902 to the fiber optic laser delivery device 306. The epoxy 908 can also be an adhesive, a bonding agent or joining compound, etc.

Figure 9B:
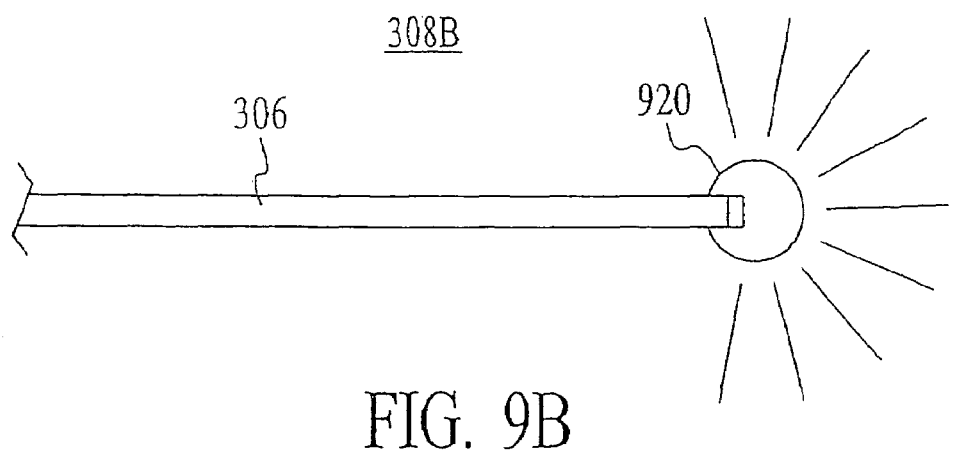
FIG. 9B is a representative view of another diffusing fiber tip according to the preferred embodiment of the method and apparatus of the present invention.

FIG. 9B is a representative view of another diffusing fiber tip 308B according to the preferred embodiment of the method and apparatus of the present invention. As shown, a small, circular diffusing bead or head 920 formed of ceramic or other suitable, appropriate material is coupled to the fiber optic laser delivery device 306. Optionally, a non-toxic, heat-resistant or other suitable epoxy 908 is used to permanently or removably mount the diffusing tip 920 to the fiber optic laser delivery device 306.

Figure 9C:
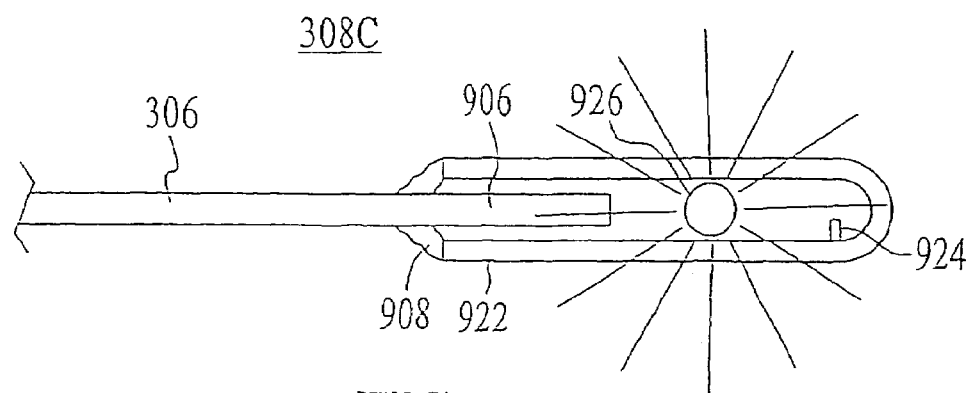
FIG. 9C is a representative view of yet another diffusing fiber tip according to the preferred embodiment of the method and apparatus of the present invention.

FIG. 9C is a representative view of yet another diffusing fiber tip 308C according to the preferred embodiment of the method and apparatus of the present invention. In this embodiment, a quartz tube 922 is placed over the distal end 906 of the optical fiber laser delivery device 306, thereby forming a sealed air chamber 924. Optionally, a spherical or other shaped diffusing ball 926 is placed within the air chamber 924 such that electromagnetic radiation directed through the fiber optic laser delivery device 306 is diffused as it is delivered from the tip 922 of the device 308C. Optionally, a non-toxic, heat resistant or other suitable epoxy 908 or other suitable attachment means is used to permanently or removably mount the quartz capillary tube 922 to the fiber optic laser delivery device 306.

Axially Directed Energy Delivery

Some methods for using laser energy to treat varicose veins provided for delivery of laser energy from the tip of the fiber optic and/or required direct contact of the vein or vessel wall by the fiber tip. Direct contact of the vein or vessel wall by the tip of the fiber optic frequently causes overheating and unintentional perforation of the vein wall, and is avoided by the apparatus and methods described herein. In addition, these previous methods have typically included use of a fiber optic having a numerical aperture (NA) of at least 0.35 to 0.40, which fibers provide an output beam having a relatively large amount of radial dispersion. This results in a great deal of unnecessary damage to healthy, non-target tissue.

The devices and methods described herein may accommodate energy delivery by optic fibers having these relatively high numerical apertures, and other structures that result in energy delivery having a relatively large amount of radial dispersion. For example, the diffusing tip fibers described herein in relation to FIGS. 9A through 9C cause laser energy to be directed laterally from the end of the fiber.

In a preferred embodiment, however, the present laser assisted methods and devices provide for delivery of laser energy in a manner that is substantially aligned with the longitudinal axis of the fiber optic and/or the vein. This longitudinally directed energy delivery may be obtained by, for example, providing optic fibers that have a relatively low numerical aperture (NA) of about 0.12 to about 0.30. Regardless of the numerical aperture value used, in this embodiment, direct contact of the vessel or vein wall by the energy-emitting optic fiber tip is preferably avoided.

Figure 14:
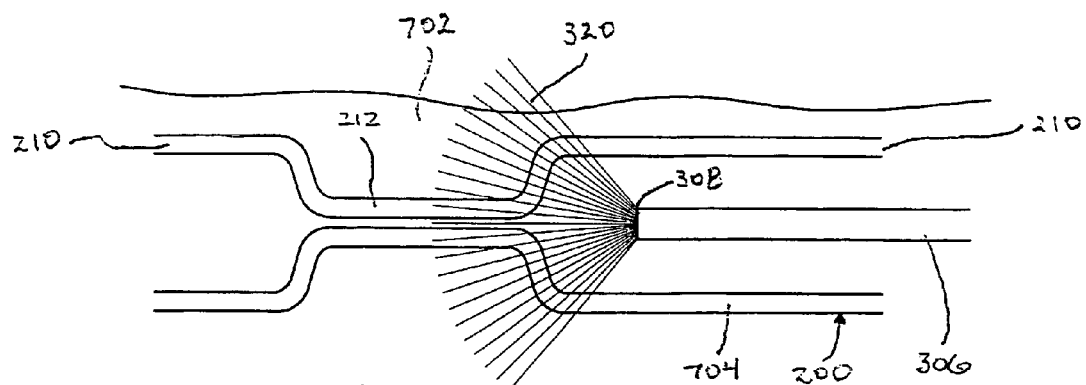
FIG. 14 is a representative view of a fiber optic catheter having a numerical aperture value of about 0.35 to about 0.40.
Figure 15:
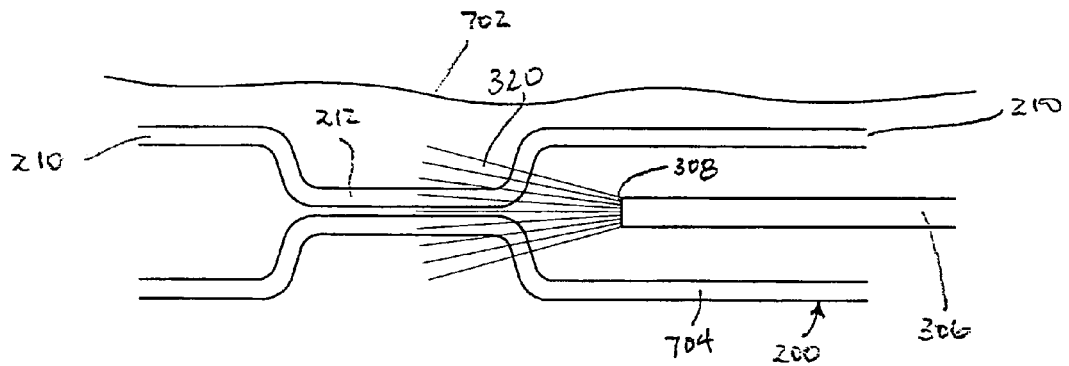
FIG. 15 is a representative view of a fiber optic catheter having a numerical aperture of about 0.12 to about 0.30.

Turning to the Figures, FIGS. 14 and 15 show an optic fiber 306 located in a vein 200 of a patient. The optic fiber 306 may be placed in the vein in the manner described previously herein, and is attached to a source of laser energy (not shown in FIGS. 14 or 15). The laser energy output from the optic fiber 306 is illustrated by the cone-shaped field 320 shown in the Figures. The optic fiber 306 shown in FIG. 14 is a conventional optic fiber having a numerical aperture (NA) of between about 0.35 to about 0.40, which creates a relatively widely dispersed energy output field 320. In contrast, the optic fiber 306 shown in FIG. 15 is one having a numerical aperture (NA) of between about 0.12 to about 0.30, which creates an energy output field 320 that is more substantially aligned with the longitudinal axis of the optic fiber 306 and the vein 200. The vein 200 includes untreated portions 210 and a treated portion 212 that has been exposed to the laser energy output from the optic fiber. The treated portion 212 shows shrinkage incurred during treatment.

The 1.2 um to 1.8 um wavelength laser energy provided by the apparatus and methods described herein is strongly absorbed by collagen making up the vessel wall 704. The present devices and methods are designed to optimize the energy delivery to the vessel wall, and to minimize exposure of non-target tissue. This is illustrated by a comparison of FIGS. 14 and 15. As shown in FIG. 14, when the laser energy output 320 from the optic fiber 306 has a conventional numerical aperture of about 0.35 to 0.40, or when it is otherwise dispersed generally radially from the tip 308 of the optic fiber 306, one result is that the energy output field 320 encounters a substantial amount of non-target tissue 702. On the other hand, as shown in FIG. 15, when the laser energy output 320 from the optic fiber 306 has a relatively lower numerical aperture of about 0.12 to about 0.30, or when the energy output 320 is more substantially aligned with the axis of the optic fiber 306, one result is that the energy output field 320 encounters a relatively smaller amount of non-target tissue 702, and a higher percentage of the target vessel wall 704.

This effect is due primarily to the orientation of the vessel wall 704 relative to the optic fiber 306. As shown in FIGS. 14 and 15, the treatment causes destruction of the endothelium cells and results in shrinkage of the vessel walls 704, causing the vessel walls 704 to collapse 212 behind the optic fiber 306 as the optic fiber 306 is withdrawn. This shrinkage causes the vessel walls 704 to be oriented generally longitudinally behind the optic fiber 306 as it is withdrawn, i.e., within a longitudinally-oriented field facing the energy-emitting tip 308 of the optic fiber 306. The substantially longitudinally oriented laser energy output field 320 obtained with the lower numerical aperture optic fiber (FIG. 15) therefore impinges upon substantially more of the vessel wall 704 material and substantially less non-target tissue 702 than does the more radially-directed energy output field 320 obtained with the higher numerical aperture optic fiber 306 (FIG. 14). This causes a substantial amount of the delivered energy to be received by and retained within the walls of the targeted vein, increasing the effectiveness of the device and method in destroying the endothelium cells of the vein and causing shrinkage of the vein wall. This also causes a relatively less amount of energy to be delivered to non-target tissue outside of the vein, decreasing the incidence of pain and surrounding tissue damage.

As discussed above, the longitudinally-directed energy output field 320 may be provided by using optic fibers having a relatively low numerical aperture (NA) of from about 0.12 to about 0.30. Optic fibers meeting this range of NA values produce a laser energy output field that is more collimated, or longitudinally-oriented (e.g., as in FIG. 15), than that produced by optic fibers having NA values of 0.35 to 0.40. The numerical aperture of an optic fiber may be controlled by adjusting the ratio of index of refraction between the core and the cladding to create varying NA values. For example, silica clad, silica core optic fibers may have NA values of from about 0.12 to about 0.22. Typical plastic clad fibers may have NA values as high as 0.35 to about 0.40. The lower the NA, the more longitudinal or collimated is the energy output from the optic fiber.

Figure 16:
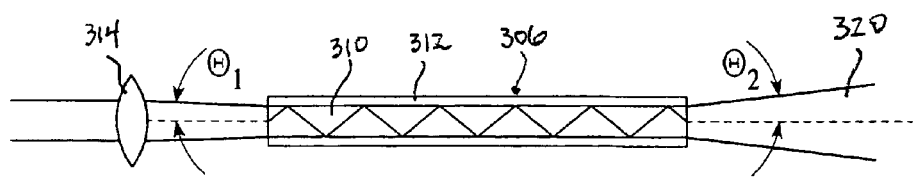
FIG. 16 is a representative view of a fiber optic catheter illustrating the launch angle of a laser input.

In addition, it is preferable to use a source of laser energy that is capable of producing a low NA output. Turning to FIG. 16, an optic fiber 306 is shown having a core 310 and a cladding layer 312. A source of laser energy (not shown) produces a laser output that is focused by a lens 314, creating a beam launch angle $\theta_1$ prior to input of the laser energy into the optic fiber 306. The laser energy is reflected and refracted as it travels the length of the optic fiber 306, and is ultimately output in an energy output field 320 having a NA value defined by the exit angle $\theta_2$ of the beam. It is preferable to provide an input beam to the optic fiber having a relatively shallow launch angle $\theta_1$ having a numerical aperture value of approximately 0.05 to about 0.12, rather than more conventional values of 0.2 or higher. With this relatively shallow launch angle, and the relatively short lengths of multimode optic fiber for the endovenous applications described herein, the apparatus tends to preserve the mode or NA of the laser launch conditions to produce a relatively collimated output beam. For example, a laser such as the Nd:YAG will produce a lower output cone angle even when it is used with higher NA fibers because the launch angle from the laser may be made shallow. On the other hand, diode lasers usually have launch NA values of 0.30 or higher and are unable to produce as collimated an output as the Nd:YAG laser.

Protective Spacer for Tip of Endovenous Catheter

The endovenous treatment methods and devices described herein utilize laser energy to treat veins such that the endothelial cells of the vessel walls 704 are damaged and collagen fibers in the vessel wall 704 are heated to the point where they permanently contract. Preferably, the vessel is occluded and ultimately resorbed. During the delivery of the laser energy, it is strongly preferred not to contact the vein or other tissue directly with the energy-emitting tip of the optic fiber delivering the laser energy, in order to prevent unwanted burning or perforation of the vein or other tissue.

In several preferred embodiments of the devices described herein, the laser energy is delivered by a fiber optic catheter 306 that is provided with a protective spacer. The spacer is preferably located on or near the tip 308 of the fiber optic catheter 306 and is constructed and dimensioned such that it prevents the vein or other tissue from coming into direct contact with the energy-emitting tip 308 of the fiber optic catheter 306 when the catheter is located in a vein or other vessel during treatment. In addition, the spacer is preferably temperature-resistant in order to prevent heat transfer from the catheter tip 308 to the vein. The spacer may also assist in shaping or moving the vein wall in a manner that increases the amount of exposure of the vein wall to the laser energy output from the fiber optic catheter 306. This result is particularly preferred in situations in which the laser energy is delivered by an optic fiber having a relatively low numerical aperture (NA) value. In those cases, proper orientation or centering of the vein wall in the energy output field of the fiber optic catheter 306 will provide increased and more uniform treatment.

The protective spacer is preferably located at or near the tip 308 of the fiber optic catheter 306, but it does not substantially interfere with the delivery of laser energy from the tip 308 of the catheter 306. For example, the spacer may be located on the outer surface of the fiber optic catheter 306 and flush with the tip 308 and therefore outside of the energy output field, or it may enclose a portion of the tip without substantially entering the energy output field. In the latter case, the amount by which the tip is enclosed will preferably relate to the numerical aperture (NA) value of the optic fiber.

Figure 17:
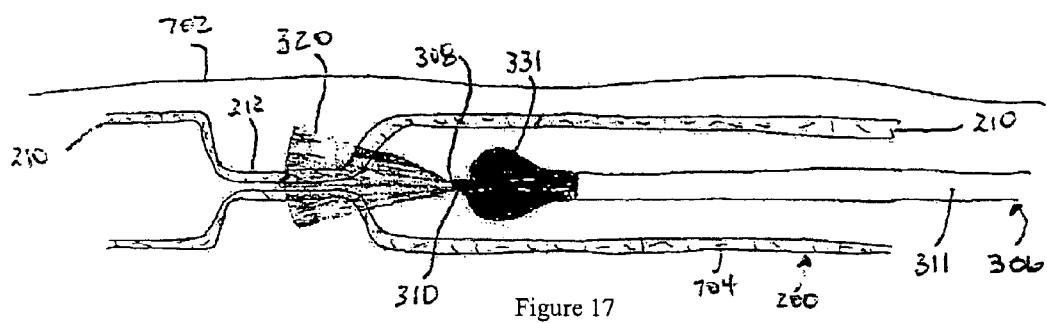
FIG. 17 is a representative view of a first embodiment of a protective spacer.

Turning to FIG. 17, a first embodiment of a protective spacer 331 is in the form of a molded body formed near the tip 308 of the fiber optic catheter 306. The fiber optic catheter 306 includes a fiber optic core 310 and a protective outer jacket 311. The fiber optic core 311 typically has a diameter of from about 150 to about 600 um, and the catheter jacket 311 typically has a diameter of from about 300 to about 800 um. The spacer 331 typically has a diameter of from about 400 um to about 1200 um. The spacer 331 is preferably formed from an epoxy, a UV setting cement, or other material suitable for molding onto the external surface of the fiber optic catheter 306. The material used to construct the molded spacer 331 is preferably opaque. The example shown in FIG. 15 is a bulb-shaped molded epoxy spacer 331. As shown in FIG. 15, the spacer 331 is formed on the outer surface of the jacket 311 of the catheter near the tip 308 of the optic fiber 310, but it does not cover the tip 308 or otherwise interfere with the delivery of laser energy from the tip 308.

Figure 18:
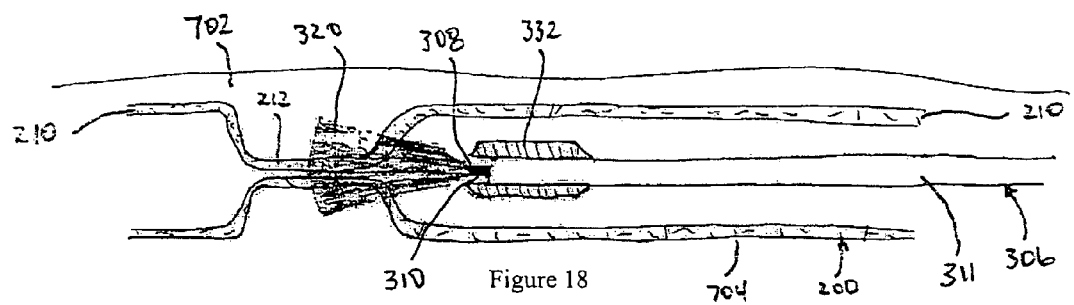
FIG. 18 is a representative view of a second embodiment of a protective spacer.

Turning to FIG. 18, a second embodiment of a protective spacer 332 is in the form of a plastic ring or sleeve attached at or near the tip 308 of the fiber optic catheter 306. The fiber optic catheter 306 includes a fiber optic core 310 and a protective outer jacket 311. The fiber optic core 310 typically has a diameter of from about 150 to about 600 um, and the catheter jacket 311 typically has a diameter of from about 300 to about 800 um. The spacer 332 typically has a diameter of from about 400 um to about 1200 um. The spacer 332 is preferably formed of a plastic, such as teflon, nylon, delrin, polyimide, or other suitable plastic material, and is preferably opaque. Alternatively, the spacer 332 may be of stainless steel or some other biocompatible metal. The spacer 332 is generally cylindrical and may be tapered or rounded at its proximal and distal ends. The spacer is glued, fused, or otherwise attached to the external surface of the jacket 311 of the catheter near the tip 308 of the optic fiber, but it does not cover the tip or otherwise interfere with the delivery of laser energy from the tip 308.

Figure 19:
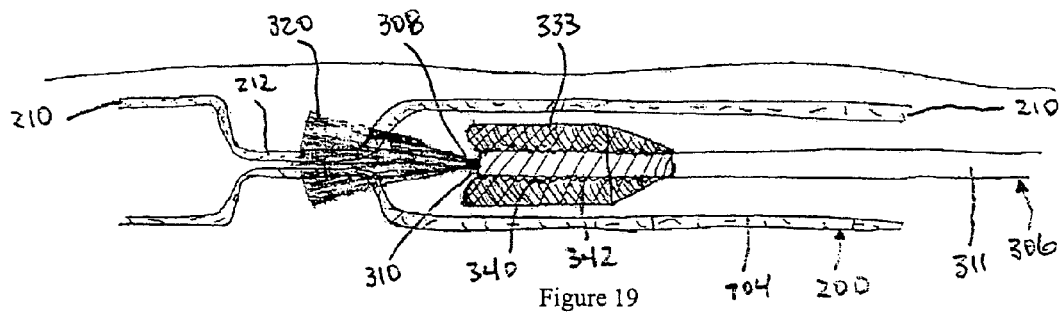
FIG. 19 is a representative view of a third embodiment of a protective spacer.

Turning next to FIG. 19, a third embodiment of a protective spacer 333 is in the form of a metal or plastic tube that is selectively detachable to the fiber optic catheter 303. The fiber optic catheter 306 includes a fiber optic core 310 and a protective outer jacket 311. The fiber optic core 310 typically has a diameter of from about 150 to about 600 um, and the catheter jacket 311 typically has a diameter of from about 300 to about 800 um. The spacer 333 typically has a diameter of from about 400 um to about 1200 um. The spacer 333 is preferably formed of a biocompatible metal such as stainless steel, or a hard plastic. The spacer 333 is generally cylindrical, preferably has a length of from about 3 to about 5 mm, and is provided with threads 340 on its internal surface that are adapted to engage threads 342 formed on the external surface of the outer jacket 311 of the fiber optic catheter 306 near its tip 308. The distal end of the spacer 333 is preferably flush with the laser-emitting tip 308 of the catheter, or it may partially enclose the tip while not interfering with the energy output field. Because the spacer 333 is selectively detachable, it may be removed for cleaning and sterilization and reused.

An additional benefit obtained by using a protective spacer 331, 332, 333 at or near the tip of a fiber optic catheter 306 is that the spacer may assist in centering the fiber optic catheter 306 in the lumen in instances where the surrounding vein 200 is not completely collapsed or the vein is too large and flattens instead of collapsing. The laser irradiation of the vein by the energy output field 320 located in front of the laser-emitting tip 308 of the fiber optic catheter is more uniform when the fiber 306 is centered within the vein 200.

The protective spacers 331, 332, 333 described herein are suitable for use on any endovenous fiber optic catheter system, regardless of the laser wavelength or other characteristics.

Rounded Tip Optic Fiber Catheter and/or Spacer

Previous methods for using laser energy to treat varicose veins included the use of an introducer sheath 300 that is inserted into a vein 200 prior to introducing the fiber optic catheter 306. The introducer sheath 300 is used in order to protect the vein from being punctured by the relatively sharp tip 308 of the fiber optic catheter 306, and to prevent the fiber optic catheter 306 from snagging or hanging up on the side of the vein during insertion. In the previous practice, the fiber optic catheter 306 was inserted into the vein through the introducer sheath 300, then the sheath 300 was withdrawn to expose the laser-emitting tip 308 of the fiber during treatment.

Figure 20:
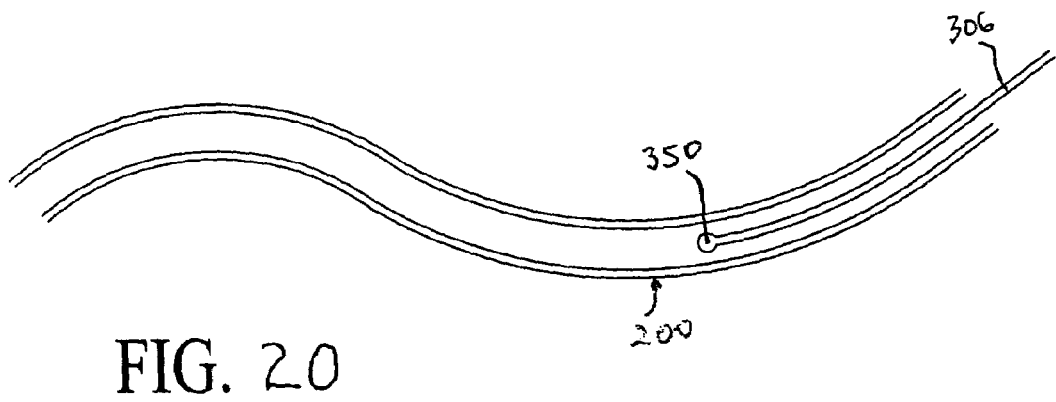
FIG. 20 is a representative view of a fiber optic catheter having a rounded tip.

The present invention includes the use of a rounded tip fiber optic catheter, as shown, for example, in FIG. 20. The rounded tip 350 is preferably formed during manufacturing of the fiber optic catheter 306 and is formed from the same fiber core material that makes up the remainder of the fiber core. The tip 350 may be spherical (as shown in FIG. 20), or it may be some other similar rounded shape that resists puncturing or snagging the vein wall.

A rounded tip fiber catheter may be inserted into a vein 200 with a greatly reduced risk of puncture because the rounded tip will slide along the vein 200, rather than digging into the vein, as the path of the vein curves. This effect is particularly pronounced when using relatively small diameter fiber catheters that otherwise more easily poke through veins and other tissue.

In addition, when treating small veins on the hands or legs it is preferable to use an introducer needle that is as small as possible and not to have to use an introducer sheath 300 for each small section of vein that is to be treated. For example, a rounded tip small diameter fiber catheter may be constructed that could be directly inserted (without an introducer sheath) into a 1 to 2 mm diameter small vein by using a needle as small as 27 gauge. This technique would produce superior results in comparison to sclerotherapy for the treatment of small veins. Moreover, a smaller needle produces less trauma to the patient and is easier to close.

In cases where a protective spacer 331, 332, 333 is used, such as those described above in relation to FIGS. 17 through 19, the present invention also includes the use of a rounded or smooth surface to be incorporated onto the distal-facing exterior portions of the of the protective spacer 331, 332, 333. The rounded or smooth exterior surface would track along the sides of the vein wall during direct insertion (without use of an introducer sheath) without catching and stopping advancement. For example, when a rounded or smooth surfaced protective spacer is used on a fiber optic catheter 306 and an introducer sheath 300 is not used, a 19 to 20 gauge needle may be used rather than a 16 to 18 gauge needle that would otherwise be necessary to accommodate a 5 French introducer sheath. This feature would save not only the expense of using an introducer sheath, but it would also save time in the operating theater that otherwise would be needed to insert the sheath.

Use of a rounded tip fiber optic catheter or a rounded or smooth surfaced protective spacer to avoid the need for an introducer sheath is particularly applicable to treatment of small veins such as found on the back of a patient's hands. It is advantageous to use as small an introducer needle as possible in these applications because the typical procedure requires multiple punctures over each visible vein on the hand. Eliminating the need for a separate introducer sheath for each puncture results in a significant decrease in time and cost for the procedure.

Fiber Optic Installed in Guidewire or Catheter

Figures 22A, 22B:
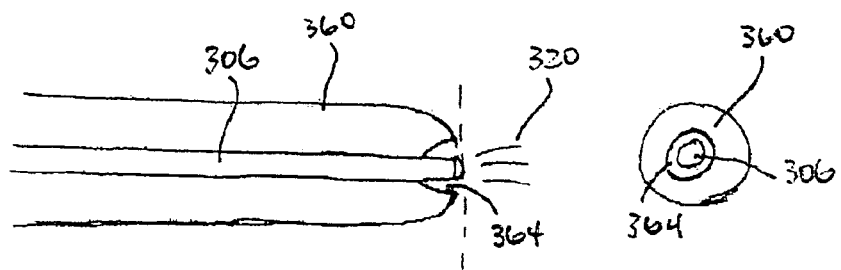
FIG. 22A is a representative view of another combination fiber optic catheter and guidewire.
FIG. 22B is an end view of the combination fiber optic catheter and guidewire of FIG. 22A.
Figure 23:
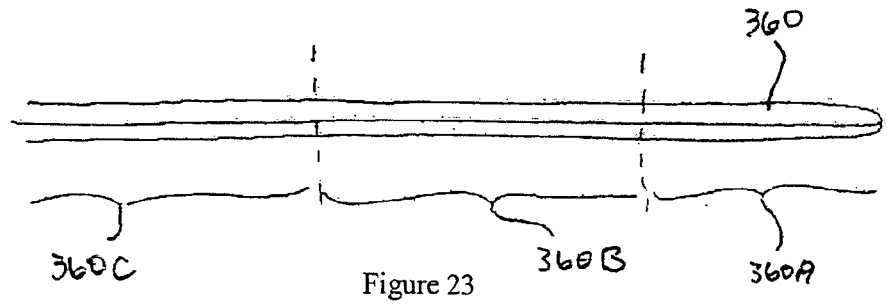
FIG. 23 is a representative view of a combination fiber optic catheter and guidewire.

Additional embodiments of devices and methods for treating varicose veins or the greater saphenous vein are illustrated in FIGS. 21 through 23. The device includes an optic fiber incorporated inside a conventional guidewire or catheter. The optic fiber is covered and protected along its length by the guidewire or catheter. The distal end of the fiber is not covered, but is open to allow laser energy to exit to treat the vein located distally of the device. Among other functions, the guidewire or catheter acts to space the fiber tip away from the vein wall in a manner similar to the protective spacers described above, thereby reducing the likelihood that the fiber tip will directly contact the vein or other tissue and cause unwanted burning or perforation.

Figures 21A, 21B:
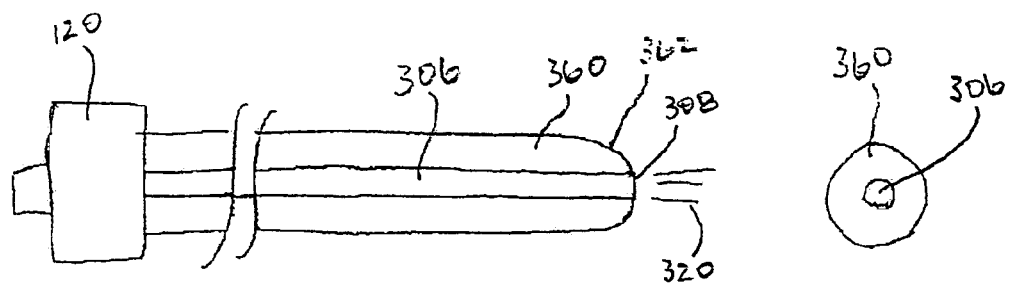
FIG. 21A is a representative view of a combination fiber optic catheter and guidewire.
FIG. 21B is an end view of the combination fiber optic catheter and guidewire of FIG. 21A.

Turning first to FIGS. 21A and 21B, a first embodiment of the endovenous treatment device includes an optic fiber 306 located concentrically within a hollow guidewire 360. The device includes a mechanism 120 for connecting to a laser console (not shown in the Figure). The optic fiber 306 may be of the same materials and construction as those described previously. The guidewire 360 is constructed of stainless steel or other suitable opaque guidewire material. The tip 308 of the optic fiber 306 is flush with the distal end of the guidewire 360, which is preferably slightly rounded 362 to enable the guidewire 360 to be inserted directly into a vein 200 if necessary, without puncturing or hanging up on the side wall of the vein. In addition, the tip 308 of the optic fiber 306 is protected from contacting the vein or other tissue by the guidewire material that extends flush with the optic fiber tip 308 at the distal end of the fiber.

An alternative embodiment of the endovenous treatment device is shown in FIGS. 22A and 22B. This embodiment is substantially similar to the first embodiment, but is provided with a recessed portion 364 at the distal end of the guidewire 360 surrounding the fiber optic tip 308. The recessed portion 364 of the guidewire provides additional exposure of the fiber optic tip 308, while still providing protection against direct contact of the tip with the vein or other tissue.

The integrated guidewire/fiber optic device provides the user with the ability to insert the treatment device in a single step, perform the treatment with the fiber tip spaced away from the vein and other tissue, and withdraw the device in a single step. In prior devices, the user was required to withdraw a protective sheath to expose the fiber optic tip inside the vein. Failure to withdraw the sheath far enough to expose the tip caused the sheath to burn and required the vein to be surgically exposed and removed. The integrated guidewire/fiber optic device described herein eliminates this undesirable result.

Figure 24:
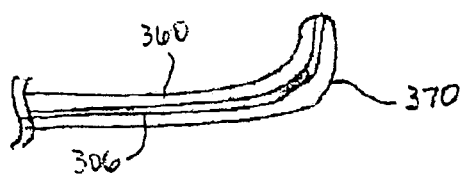
FIG. 24 is a representative view of a combination fiber optic catheter and guidewire having a curved distal portion.
Figure 25:
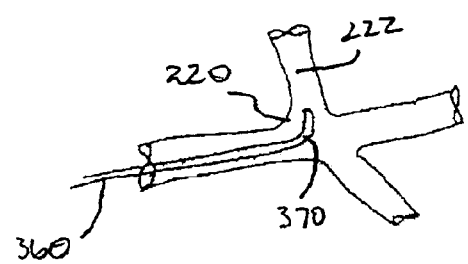
FIG. 25 is a representative view of a combination fiber optic catheter and guidewire inserted into a blood vessel illustrating a process of steering the device into a branch vessel.

In addition, providing the optic fiber 306 within the interior of a hollow guidewire 360 provides the user with the ability to steer or guide the optic fiber through curved or tortuous veins. Guidewires are conventionally used to perform an initial penetration to a treatment site because they are designed with varying degrees of stiffness and flexibility from the proximal to the distal ends of the wire. See, for example, FIG. 23, which designates sections of an exemplary guidewire having varying physical properties. In the example, a first section 360A near the distal end of the guidewire will typically be made to have a sufficient rigidity to allow the distal end of the guidewire to pass through curves or other obstacles. A second section 360B of the guidewire is preferably made less rigid and more flexible to enable the guidewire to flex and bend. A third section 360C is again more rigid to provide strength sufficient to push the guidewire along its path through the patient's vasculature. This combination of physical properties allows the user to push the guidewire 360 through obstacles, around bends, and past peripheral junctions in the venous system. For example, as shown in FIG. 24, the guidewire 360 and internal optic fiber 306 may be provided with a flexible distal portion 370 for branch access or to accommodate vein tortuosity. Thus, as shown for example in FIG. 25, when the device encounters a venous junction 220, the device can be steered into the appropriate branch 222 to access the target site. Combining a concentric optic fiber within a hollow guidewire allows the user to take advantage of these properties of the guidewire and to insert the optic fiber to the treatment site. Additionally, the physical properties of the guidewire will allow external torque to rotate the tip to the desired position to access sidebranches or to navigate curves in the vessel.

In an alternative embodiment, a fiber-catheter combination may be formed by extrusion or other deposition method of Nylon, Nylon 12, PTFE, FEP, or other conventional catheter materials onto an optic fiber. The structure would be identical to that shown in FIGS. 21A-B, 22A-B, and 23-25, except that one or more of these catheter materials would be substituted for the hollow guidewire 360. The mechanical properties of such a fiber-catheter may be designed to provide performance equivalent to that of the guidewire embodiment described above.

Echogenic Marker

One or more echogenic markers may be provided on a portion of the endovenous treatment device in order to assist the user in introducing and using the device under ultrasound visualization. It is conventional to use Doppler and duplex ultrasound imaging equipment to assist in endovenous procedures. The visibility of the devices described herein is enhanced by the provision of an echogenic marker.

Figure 26:
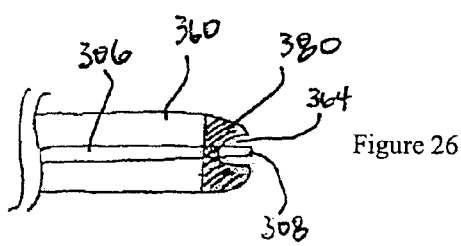
FIG. 26 is a representative view of a combination fiber optic catheter and guidewire including an echogenic marker.
Figure 27:
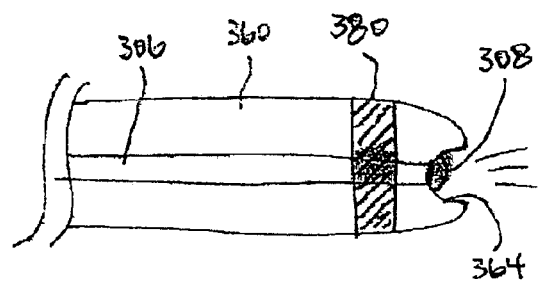
FIG. 27 is a representative view of a combination fiber optic catheter and guidewire including another echogenic marker.

Turning to FIG. 26, a first embodiment of an endovenous treatment device having an echogenic marker 380 is shown as a device having an internal fiber optic core 306 surrounded by a hollow guidewire 360. The echogenic marker 380 is located at the distal end of the device, replacing a portion of the guidewire 360. Turning to FIG. 27, a second embodiment of the device includes a band of echogenic material 380 located near the distal end of the device, but proximal of the tip 308. The marker portion 380 of the device may be placed on or in other locations on the device, or at multiple locations, as desired for enhancing visualization of the device.

The echogenic material 380 used to make up the marker is preferably metal, ceramic, or other materials that create an acoustic reflection when inserted within or in contact with tissue. The enhanced visibility created by the echogenic marker offers the advantage of being able to monitor the insertion and treatment processes in real time.

As a further alternative embodiment, where a protective spacer 331, 332, 333 is used, such as those described above in relation to FIGS. 17 through 19, the spacer may be formed of an echogenic material, or an echogenic marker may be formed on a portion of the spacer. In either case, ultrasound visualization is enhanced by provision of an echogenic marker in association with the protective spacer.

Experimental Results

A novel endoluminal laser was evaluated in 12 incompetent greater saphenous veins in 11 patients.

Method Overview: Twelve incompetent greater saphenous veins in 11 patients were treated with a 1320 nm "continuous" Nd:YAG laser at 5 W with an automated pull-back system at 1 mm/sec. Patients were examined at 1 week, 3, 6 and 9 months post-operatively. Ten treated veins were examined histologically.

Brief Results: Full thickness vein wall thermal damage occurred in all patients without evidence for vessel perforation. No post-operative complications or pain was noted in any patient. All patients had complete disappearance of the incompetent GSV with resolution of all pre-operative symptoms.

Brief Conclusion: The 1320 nm Nd:YAG laser is safe and effective for endovascular ablation of the incompetent greater saphenous vein.

| Method: Patient characteristics are found in Table 1. |
| --- |
| 11 patients 12 Great Saphenous Veins |
| 10 female 1 male |
| Average Age: 50 (19-78) |
| 12/12 legs had varicose and reticular veins |
| 12/12 legs had reflux > 1. see through the saphenofemoral junction down the great saphenous vein |
| 12/12 had leg pain |
| 2/12 had leg edema |
| Great Saphenous vein diameter to saphenofemoral junction while patient is standing 5.5-12 mm (Ave. 8.4 mm) |

Table 1 Patient Characteristics:

A 550 um quartz fiber is inserted into the vein through an externalization approach as previously described and threaded up to the saphenofemoral junction. The position of the fiber within the vein is noted by observing the red aiming beam of the laser as it is emitted from the tip of the catheter as well as through Duplex evaluation. The catheter is connected to a motorized pull back device. The procedure begins by starting the pull back for about 2 or 3 mm and then turning the laser on in a near continuous mode at 5 W at 167 mJoules given at a repetition rate of 30 Hz. All laser fibers were withdrawn with a motorized pull-back system at a rate of 1 mm/second.

The average length of treated GSV was 1.7.45+/−3 cm. Average fluence utilized was 755 Joules over 160+/−20 seconds for an average of 4.7 J/sec. Immediately after the veins were lasered, the distal 3 cm was excised, the proximal portion ligated with 3/0 vicryl suture and placed in formaldehyde for histopathologic processing and evaluation. Nine veins were evaluated by a dermatopathologist blinded to the purpose and parameters of the experiment.

Patients were seen back at 1 day, 1 week, 1, 3, 6, and 9, months post-operatively for Duplex examination. This examination was performed by a physician not involved in the surgical procedure.

Experimental Results:

All patients tolerated the procedure well without any noticeable pain or discomfort. All patients had an unremarkable post-operative course without any pain. Bruising over the course of the treated vein occurred in 2 of the 12 treated legs and resolved within 10-14 days. No evidence of superficial thrombophlebitis occurred.

Three patients with four treated legs were followed for 9 months, three patients were followed for 6 months and 5 patients were followed for 3 months.

All patients remarked on the complete resolution of preoperative pain. Of the two patients with pedal edema, one patient had total resolution of the pedal edema. The other patient had a 75% reduction in pedal edema.

Duplex examination of the treated GSV segment demonstrated a non-compressible totally occluded vessel for 3r5 months-post-operatively in every patient. At 3 months, the thrombotic GSV was 1-4 mm in diameter smaller (approximately 50%). At 6 months, the GSV could not be identified in any patient.

Figure 11:
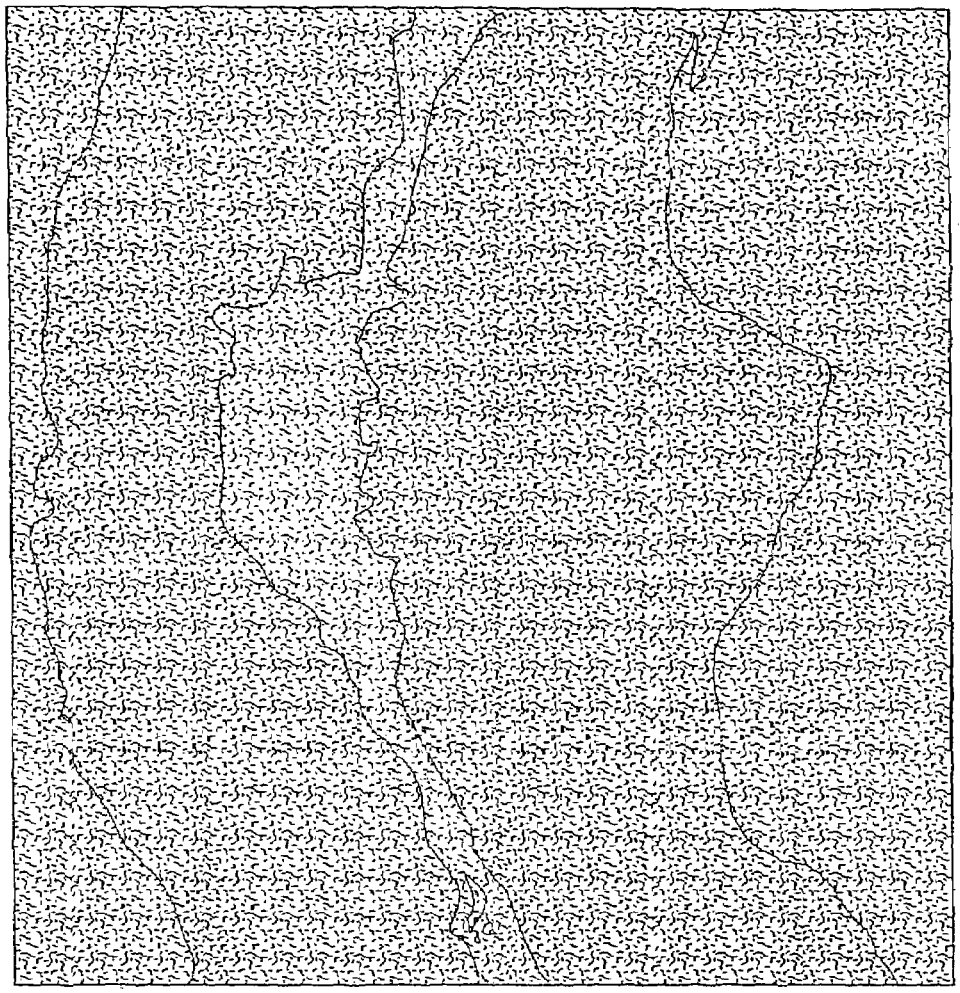
FIG. 11 is a photograph of experimental results showing the distal greater saphenous vein immediately after treatment with a 1320 nm Nd:YAG laser.

FIG. 11 is a photograph of experimental results showing the distal greater saphenous vein immediately after treatment with a 1320 nm Nd:YAG laser. Table 2 describes the extent of thermal damage into the vein wall in mm of amorphous amphophilic material. In addition, the layers of vein wall exhibiting thermal damage were described. Full thickness vein wall damage occurred in all specimens.

TABLE 2

Perioperative Diameter of the Great Saphenous Vein and Extent of Thermal Damage from intravascular 1320 nm Laser

| Pre-operative Diameter | Thickness of thermal damage (amorphouse amphophilic material)(mm) |
|---|---|
| 8.0 mm | 0.8 mm full thickness vein wall damage |
| 9.0 mm | Full thickness damage 1 mm in depth including hyperchromasia or loss of enfothelial nuclei, and subendothelial necrosis |
| 8.0 mm | Full thickness damage of the vein wall to 0.33 mm of endothelial nuclei and subendothelial necrosis |
| 5.5 mm | Full Thickness subendothelial damage to 0.9 mm with hyperchromasia of endothelial cells |
| 8.2 mm | 0.75 mm full thickness vein wall damage |
| 8.3 mm | 0.74 mm full thickness vein wall damage |
| 10 mm | 0.6 mm full thickness vein wall damage |
| 7.7 mm | 0.7 mm full thickness vein wall damage |
| 8 mm | 0.8 mm full thickness vein wall damage |

Discussion: Optical absorption curves show that the primary absorbing, chromophore in a vein for the 810, 940 and 1064 nm laser wavelengths is hemoglobin. When a vein is drained of blood and these lasers are used a majority of the laser energy is transmitted through the vessel wall to heat surrounding tissue. The 1320 nm laser wavelength is ideally suited to penetrate the small amount of remaining blood in the vessel and is much more strongly absorbed in the vessel wall by collagen. Most of the energy is concentrated in the wall for heating and shrinkage. This study demonstrates that the 1320 nm-Nd:YAG laser with an automated pull-back system is safe and effective for endovascular laser destruction of the GSV.

Unless defined otherwise, all technical and scientific terms used herein have the same meaning as commonly understood by one of ordinary skill in the art to which the present invention belongs. Although any methods and materials similar or equivalent to those described can be used in the practice or testing of the present invention, the preferred methods and materials are now described. All publications and patent documents referenced in the present invention are incorporated herein by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

We claim:

1. A method for treating a varicose vein using laser energy to heat and shrink the wall of the vein, comprising the steps of:
   inserting a laser-emitting member into a varicose vein, said laser-emitting member comprising an optic fiber having a non-expandable spacer coupled to said fiber near its distal end, said spacer having an outer surface capable of contacting an inner wall of the blood vessel to substantially prevent the distal end of said optic fiber from contacting the inner wall of the varicose vein,
   placing the laser-emitting member at a treatment site within the varicose vein, and
   emitting laser energy having a wavelength in the range of about 1.2 um to about 2.2 um into the varicose vein through said laser-emitting member to preferentially heat the water in said vein, while longitudinally moving the inserted optic fiber and spacer such that the spacer positions the distal end of the optic fiber away from the inner wall of the varicose vein to substantially prevent the distal end of the optic fiber from contacting the inner wall of the varicose vein.

2. The method of claim 1, wherein said laser energy has a wavelength that falls within the range of from about 1.2 um to about 1.8 um.

3. The method of claim 1, wherein said laser energy has a wavelength of about 1.32 um.

4. A method for treating a varicose vein using laser energy to heat and shrink the wall of a varicose vein, comprising the steps of:
   inserting a laser-emitting member into a varicose vein, said laser-emitting member comprising an optic fiber having proximal and distal ends and having an energy emitting tip at its distal end, said optic fiber further having a non-expandable spacer attached to its distal end, said spacer adapted to substantially prevent the tip of said optic fiber from directly contacting the varicose vein during treatment,
   inserting the laser-emitting member into the varicose vein to locate it at a treatment site, and
   emitting laser energy having a wavelength of about 1.2 um to about 2.2 um into the varicose vein through said laser-emitting member while longitudinally moving the inserted optic fiber and spacer while continuing to deliver energy sufficient to close said vein such that the spacer positions the distal end of the optic fiber away from the inner wall of the varicose vein to substantially prevent the distal end of the optic fiber from contacting the inner wall of the varicose vein.

5. The method of claim 4, wherein said laser energy has a wavelength of about 1.32 um.

6. The method of claim 4, wherein said laser energy has a wavelength that falls within the range of from about 1.2 um to about 1.8 um.

7. The method of claim 4, wherein said laser energy has a wavelength that falls within the range of from about 1.9 um to about 2.2 um.

8. The method of claim 4, wherein said optic fiber has a numerical aperture value of about 0.12 to about 0.30.

9. An endovascular treatment method for treating varicose veins comprising:
   inserting into a varicose vein a non-expandable polymeric plastic spacer coupled to an optic fiber having a distal end, positioning the spacer such that the distal end of the optic fiber within the varicose vein is prevented from contacting the wall of the varicose vein, and delivering energy having a wavelength of about 1.2 um to about 2.2 um through the distal end of the inserted fiber to preferentially heat the water in the vein wall to cause closure of the varicose vein.

10. An endovascular treatment method comprising:

inserting into a blood vessel a non-expandable spacer arranged near a distal end of an optical fiber, the spacer comprising polymeric plastic, and applying laser energy having a wavelength of about 1.2 um to about 2.2 um through the distal end of the optical fiber while longitudinally moving the inserted optical fiber and spacer such that the spacer positions the distal end of the optical fiber away from the inner wall of the vessel to prevent the distal end of the optical fiber from contacting the inner wall of the blood vessel, the application of laser energy preferentially heating the water in the vein wall thereby causing closure of the blood vessel.

* * * * *